United States Patent
Esashi et al.

(10) Patent No.: US 10,806,749 B2
(45) Date of Patent: Oct. 20, 2020

(54) TLR INHIBITORY OLIGONUCLEOTIDES AND THEIR USE

(71) Applicant: SBI Biotech Co., Ltd., Tokyo (JP)

(72) Inventors: Eiji Esashi, Tokyo (JP); Koji Ishida, Tokyo (JP); Takumi Hosozawa, Tokyo (JP); Megumi Okuyama, Tokyo (JP); Ayumi Kotaki, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 0 days.

(21) Appl. No.: 16/064,926

(22) PCT Filed: Dec. 22, 2016

(86) PCT No.: PCT/JP2016/088418
§ 371 (c)(1),
(2) Date: Jun. 21, 2018

(87) PCT Pub. No.: WO2017/111045
PCT Pub. Date: Jun. 9, 2017

(65) Prior Publication Data
US 2019/0008888 A1    Jan. 10, 2019

(30) Foreign Application Priority Data
Dec. 25, 2015   (JP) .................. 2015-255008

(51) Int. Cl.
| | |
|---|---|
| *C12N 15/11* | (2006.01) |
| *A61K 31/7125* | (2006.01) |
| *C12N 15/117* | (2010.01) |
| *A61K 45/06* | (2006.01) |
| *A61P 3/04* | (2006.01) |

(52) U.S. Cl.
CPC .......... *A61K 31/7125* (2013.01); *A61K 45/06* (2013.01); *A61P 3/04* (2018.01); *C12N 15/117* (2013.01); *C12N 2310/17* (2013.01); *C12N 2310/315* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 8,030,289 B2 | 10/2011 | Wang et al. | |
| 2006/0292566 A1* | 12/2006 | Frazer ..................... | A61P 35/00 435/6.11 |
| 2010/0035972 A1 | 2/2010 | Wang et al. | |

FOREIGN PATENT DOCUMENTS

| | | | |
|---|---|---|---|
| EP | 2 154 144 A1 | 2/2010 | |
| JP | 5011520 B2 | 6/2012 | |
| WO | WO 2005/101968 | 11/2005 | |
| WO | WO 2006/105361 | 10/2006 | |
| WO | 2014/082254 | 6/2014 | |
| WO | WO-2015120322 A1 * | 8/2015 | |

OTHER PUBLICATIONS

Baldwin (Jr) et al., "The NF-κB and IκB Proteins: New Discoveries and Insights", Annu Rev Immunol, 1996, 14, 649-683.
Mutisya et al., "Amides are excellent mimics of phosphate internucleoside linkages and are well tolerated in short interferring RNAs", Nucleic Acids Research, 2014, 45, 6542-6551.
Sharma et al., "Antisense oligonucleotides: modifications and clinical trials", Med. Chem. Commun. 2014, 5, 1454-1471.
Wellman, et al., "The evolution of human anti-double-stranded DNA autobodies", Proc Natl Acad Sci USA, 2005, 102, 9258-63.
Zhang et al., "Structure—activity relationship of a guanine-free ligodeoxynucleotide as immunipotent inhibitor", International Immunopharmacol, 2012, 446-453.
Dirin et al., "Influence of diverse chemical modifications on the ADME characteristics and toxicology of antisense oligonucleotides," Expert Opinion on Biological Therapy, 2013, 13(6):875-888.
European Extended Search Report in European Patent Application No. 16878931.1, dated Jul. 18, 2019, 7 pages.
International Search Report and Written Opinion in International Application No. PCT/JP2016/088418, dated Feb. 28, 2017, 9 pages.
[No Author Listed], "Guidance for Industry, Estimating the Maximum Safe Starting Dose in Initial Clinical Trials for Therapeutics in Adult Healthy Volunteers," U.S. Department of Health and Human Services Food and Drug Administration, Center for Drug Evaluation and Research (CDER), Pharmacology and Toxicology, Jul. 2005, 30 pages.
Barrat, et al., "Nucleic acids of mammalian origin can act as endogenous ligands for Toll-like receptors and may promote systemic lupus erythematosus," J. Exp. Med., 2005, 202:1131-1139.
Boulé et al., "Toll-like Receptor 9-Dependent and -Independent Dendritic Cell Activation by Chromatin-Immunoglobulin G Complexes," J. Exp. Med., 2004, 199:1631-1640.
Bu.edu [Online], "Diseases," The Gilmore Lab, Boston University Biology, [Retrieved on Nov. 4, 2015], retrieved from: URL<http://www.bu.edu/nf-kb/physiological-mediators/diseases/>, 19 pages.
Burdick et al., "Sequence motifs associated with hepatotoxicity of locked nucleic acid—modified antisense oligonucleotides," Nuc. Acid Res., 2014, 42:4882-4891.

(Continued)

*Primary Examiner* — Dana H Shin
(74) *Attorney, Agent, or Firm* — Fish & Richardson P.C.

(57) ABSTRACT

The inhibitory oligonucleotides with partial phosphorothioation with reduced toxicity strongly block NF-kB activation induced by TLR9 agonists and TLR7/8 agonists. The production of proinflammatory cytokines, such as interleukin-6 (IL-6) and tumor necrosis factor alpha (TNFa), is inhibited by the inhibitory-oligonucleotides. Interferon (IFN) production from human PBMC induced by TLR9 agonist is prevented by the inhibitory-oligonucleotides. These oligonucleotides can be used as a remedy for the treatment of immune-mediated disorders such as rheumatoid arthritis, systemic lupus erythematosus (SLE), sepsis, multiple organ dysfunction syndromes and inflammatory cytokine-mediated inflammatory disease.

6 Claims, 6 Drawing Sheets
Specification includes a Sequence Listing.

(56) References Cited

OTHER PUBLICATIONS

Christensen et al., "Toll-like Receptor 7 and TLR9 Dictate Autoantibody Specificity and Have Opposing Inflammatory and Regulatory Roles in a Murine Model of Lupus," Immunity, 2006, 25:417-428.
Davidson et al., "Autoimmune Diseases," New Engl. J. Med., 2001, 345:340-350.
Deleavey et al., "Designing Chemically Modified Oligonucleotides for Targeted Gene Silencing," Chemistry & Biology, 2012, 19,:937-954.
Delgado-Vega et al., "Genetic associations in type I interferon related pathways with autoimmunity," Arthritis Research & Therapy, 2010, 12(Suppl 1):S2.
Espat et al., "PEG-BP-30 Monotherapy Attenuates the Cytokine-Mediated Inflammatory Cascade in Baboon *Escherichia coli* Septic Shock," J. Surg. Res., 1995, 59:153-158.
Freier et al., "The ups and downs of nucleic acid duplex stability: structure-stability studies on chemically-modified DNA:RNA duplexes," Nuc. Acid Res., 1997, 25:4429-4443.
Gambuzza et al., "Targeting Toll-like receptors: Emerging therapeutics for multiple sclerosis management," J. Neuroimmunol., 2011, 239:1-12.
Gilliet et al., "Plasmacytoid dendritic cells: sensing nucleic acids in viral infection and autoimmune diseases," Nat. Rev. Immunol., 2008, 8:594-606.
Goldsby et al., Immunology, Fifth Edition, W.H. Freeman and Company, 2003, Chapters 16 and 21, 42 pages.
Hagedorn et al., "Hepatotoxic Potential of Therapeutic Oligonucleotides Can Be Predicted from Their Sequence and Modification Pattern," Nuc. Acid Ther., 2013, 23:302-310.
Hatemi et al., "Behcet's syndrome: a critical digest of the 2014-2015 literature," Clin. Exp. Rheumatol., 2015, 33(6 Suppl 94):3-14.
Henry et al., "Correlation of Toxicity and Pharmacokinetic Properties of a Phosphorothioate Oligonucleotide Designed to Inhibit ICAM-1," Toxicol. Pathol., 1999, 28:95-100.
Ito et al., "Specialization, kinetics, and repertoire of type 1 interferon responses by human plasmacytoid predendritic cells," Blood, 2006, 107: 2423-2431.
Klinman, "Immunotherapeutic Uses of CpG Oligodeoxynucleotides," Nat. Rev. Immunol., 2004, 4:249-258.
Krieg, "Therapeutic potential of Toll-like receptor 9 activation," Nature Reviews Drug Discovery, 2006, 5:471-484.
Kuwahara et al., "Molecular Evolution of Functional Nucleic Acids with Chemical Modifications," Molecules, 2010, 15:5423-5444.
Leadbetter et al., "Chromatin—IgG complexes activate B cells by dual engagement of IgM and Toll-like receptors," Nature, 2002, 416:603-607.
Liew et al., "Negative Regulation of Toll-Like Receptor-Mediated Immune Responses," Nature Reviews Immunology, 2005, 5:446-458.
Liu et al., "Emerging role of toll-like receptors in the control of pain and itch," Neurosci. Bull., 2012, 28:131-144.
Liu et al., "Toll-Like Receptors and Itch," Chapter 14, Itch: Mechanisms and Treatment, Carstens E, Akiyama T, editors, 2014, CRC Press/Taylor & Francis, 11 pages.
Maeda et al., "A Novel Plasmacytoid Dendritic Cell Line, CAL-1, Established from a Patient with Blastic Natural Killer Cell Lymphoma," Int. J. Hematol., 2005, 81:148-154.
Marshall et al., "Toxoplasma gondii Triggers Granulocyte-Dependent Cytokine-Mediated Lethal Shock in D-Galactosamine-Sensitized Mice," Infect. Immun., 1998, 66:1325-1333.
Miyazawa et al., "Constitutive Transcription of the Human Interleukin-6 Gene by Rheumatoid Synoviocytes: Spontaneous Activation of NF-κB and CBF1," Am. J. Pathol., 1998, 152:793-803.
Monteith et al., "Evaluation of the Renal Effects of an Antisense Phosphorothioate Oligodeoxynucleotide in Monkeys," Toxicol. Pathol., 1999, 27:307-317.
Neurath et al., "Cytokine Gene Transcription by NF-κB Family Members in Patients with Inflammatory Bowel Disease," Ann. NY Acad. Sci., 1998, 859:149-159.
Patel et al., "A novel protective role for the innate immunity Toll-Like Receptor 3 (TLR3) in the retina via Stat3," Mol. Cell. Neurosci., 2014, 63:38-48.
Peter et al., "Characterization of suppressive oligodeoxynucleotides that inhibit Toll-like receptor-9-mediated activation of innate immunity," Immunology, 2008, 123:118-128.
Schottelius et al., "Interleukin-10 Signaling Blocks Inhibitor of κB Kinase Activity and Nuclear Factor κB DNA Binding," J. Biol. Chem. 1999, 274:31868-31874.
Slifka et al., "Clinical implications of dysregulated cytokine production," J. Mol. Med., 2000, 78:74-80.
Smith, "Toll-like receptors in kidney disease," Curr. Opin. Nephrol. Hypertens, 2009, 18:189-196.
Stein et al., "Physicochemical properties of phosphorothioate oligodeoxynucleotides," Nuc. Acid Res., 1988, 16:3209-3221.
Sun et al., "A human microsatellite DNA-mimicking oligodeoxynucleotide with CCY repeats negatively regulates TLR7/9-mediated innate immune responses via selected TLR pathways," Clin. Immunol., 2010, 134:262-276.
Tak et al., "NF-κB: a key role in inflammatory diseases," J. Clin. Invest., 2001, 107:7-11.
Tang et al., "Differential neutrophil activation in viral infections: Enhanced TLR-7/8-mediated CXCL8 release in asthma," Respirology, 2016, 21:172-179.
Wang et al., "The cytokine storm and factors determining the sequence and severity of organ dysfunction in multiple organ dysfunction syndrome," Am. J. Emerg. Med., 2008, 26,:711-715.
Writing Committee of the World Health Organization (WHO) Consultation on Human Influenza A/H5, "Avian influenza A (H5N1) infection in humans," N. Engl. J. Med., 2005, 353:1374-1385.
Communication pursuant to Article 94(3) EPC in European Patent Application No. 16878931.1, dated May 29, 2020, 4 pages.

* cited by examiner

[Fig. 1]
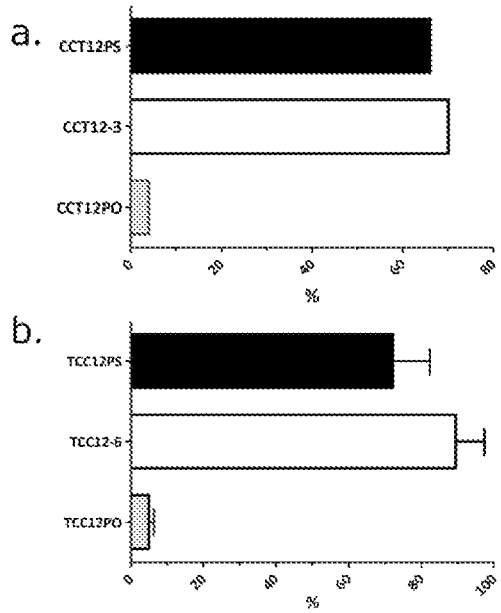
[Fig. 2a]
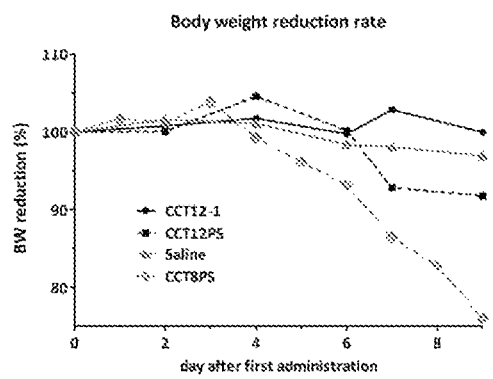
[Fig. 2b]
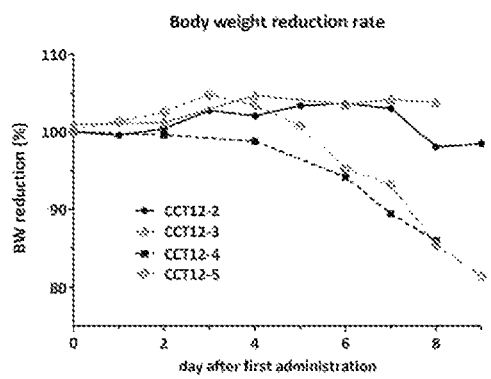

[Fig. 2c]
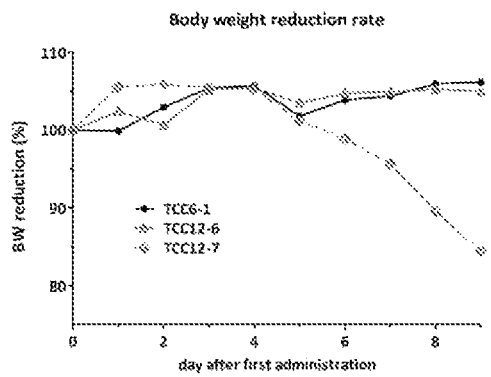
[Fig. 2d]
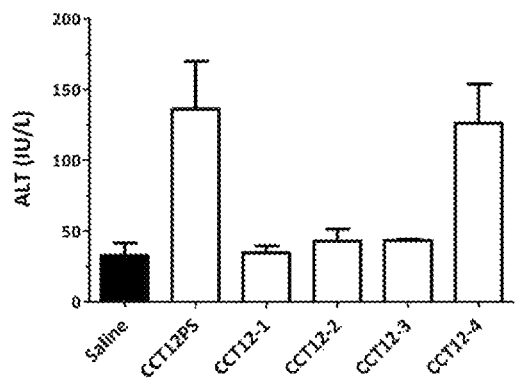
[Fig. 2e]
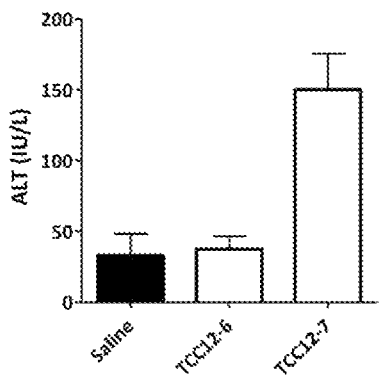

[Fig. 3a]
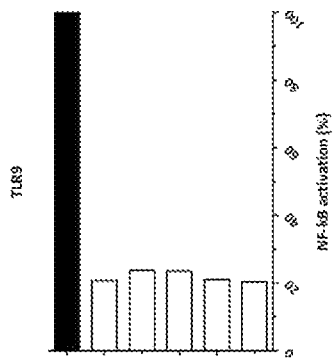
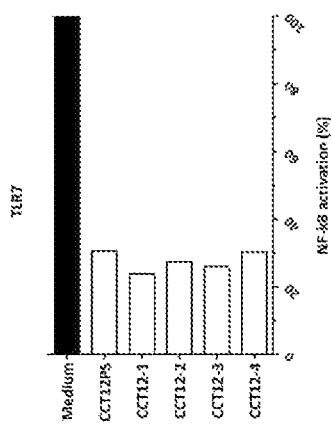
[Fig. 3b]
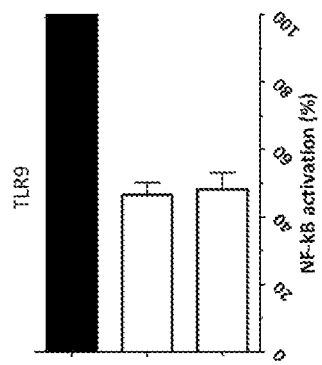
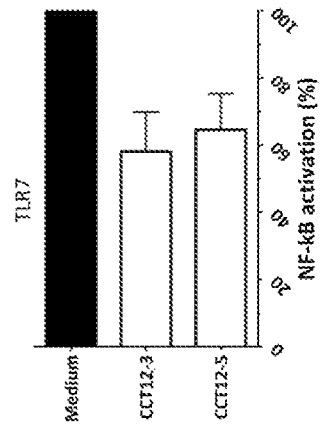

[Fig. 3c]
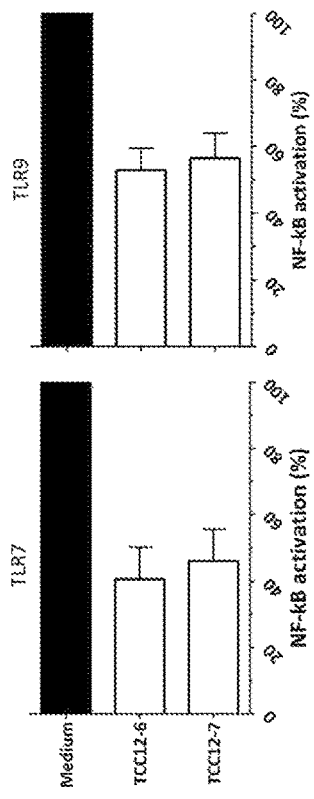
[Fig. 4a]
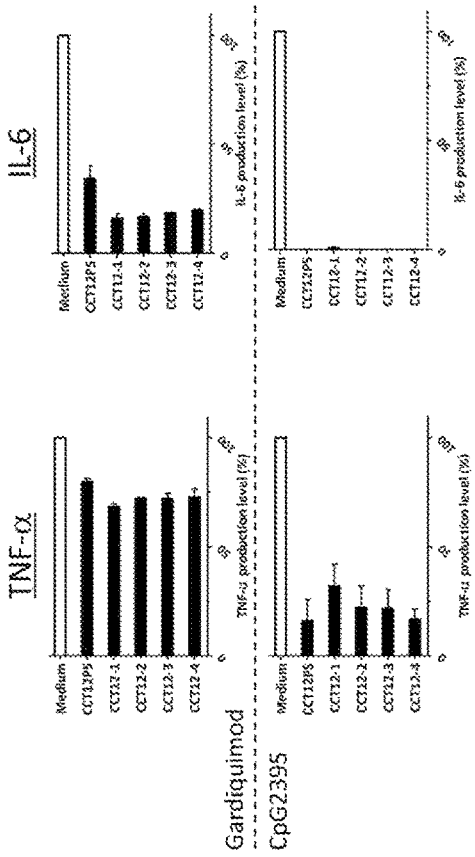

[Fig. 4b]
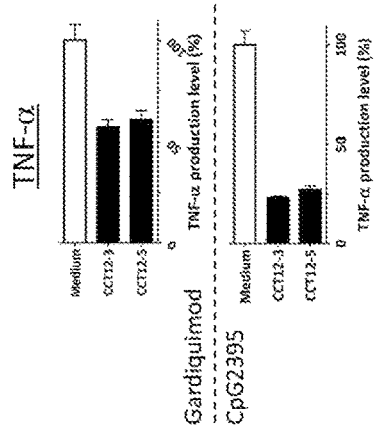
[Fig. 4c]
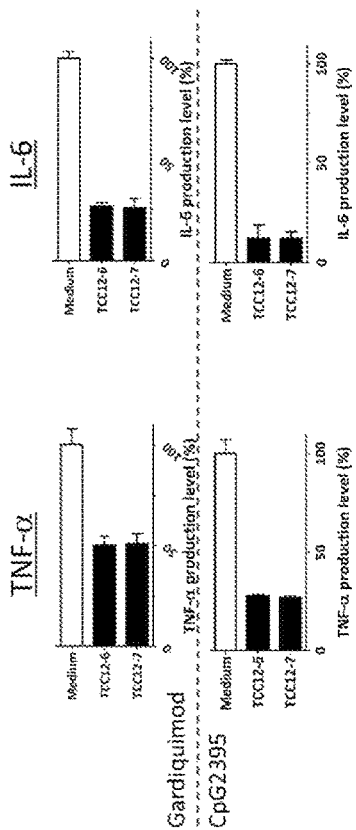

[Fig. 5]
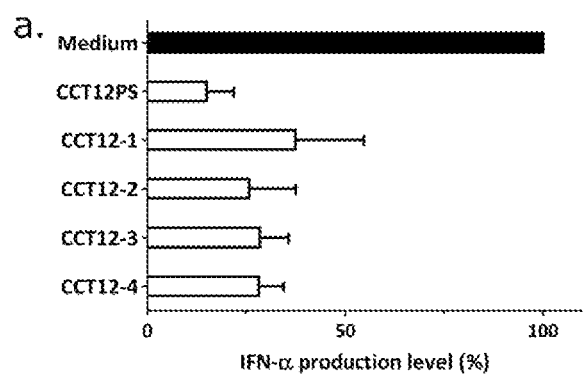
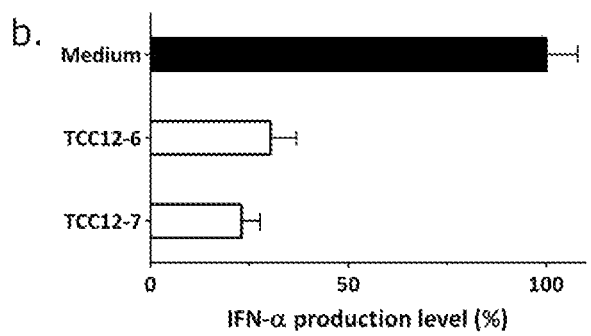

SEQUENCE LISTING

<160> NUMBER OF SEQ ID NOS: 50

<210> SEQ ID NO 1
<211> LENGTH: 18
<212> TYPE: DNA
<213> ORGANISM: Artificial Sequence
<220> FEATURE:
<223> OTHER INFORMATION: (CCT)6 inhibitory oligonucleotide

<400> SEQUENCE: 1
cctcctcctc ctcctcct        18

<210> SEQ ID NO 2
<211> LENGTH: 21
<212> TYPE: DNA
<213> ORGANISM: Artificial Sequence
<220> FEATURE:
<223> OTHER INFORMATION: (CCT)7 inhibitory oligonucleotide

<400> SEQUENCE: 2
cctcctcctc ctcctcctcc t        21

<210> SEQ ID NO 3
<211> LENGTH: 24
<212> TYPE: DNA
<213> ORGANISM: Artificial Sequence
<220> FEATURE:
<223> OTHER INFORMATION: (CCT)8 inhibitory oligonucleotide

<400> SEQUENCE: 3
cctcctcctc ctcctcctcc tcct        24

<210> SEQ ID NO 4
<211> LENGTH: 25
<212> TYPE: DNA
<213> ORGANISM: Artificial Sequence
<220> FEATURE:
<223> OTHER INFORMATION: (CCT)8C inhibitory olionucleotide

<400> SEQUENCE: 4
cctcctcctc ctcctcctcc tcctc        25

<210> SEQ ID NO 5
<211> LENGTH: 26
<212> TYPE: DNA
<213> ORGANISM: Artificial Sequence
<220> FEATURE:
<223> OTHER INFORMATION: (CCT)8CC inhibitory oligonucleotide

<400> SEQUENCE: 5
cctcctcctc ctcctcctcc tcctcc        26

<210> SEQ ID NO 6
<211> LENGTH: 27
<212> TYPE: DNA
<213> ORGANISM: Artificial Sequence
<220> FEATURE:
<223> OTHER INFORMATION: (CCT)9 inhibitory oligonucleotide

<400> SEQUENCE: 6
cctcctcctc ctcctcctcc tcctcct        27

<210> SEQ ID NO 7
<211> LENGTH: 28
<212> TYPE: DNA
<213> ORGANISM: Artificial Sequence
<220> FEATURE:
<223> OTHER INFORMATION: Inhibitory oligonucleotide

<400> SEQUENCE: 7
cctcctcctc ctcctcctcc tcctcctc        28

<210> SEQ ID NO 8
<211> LENGTH: 29
<212> TYPE: DNA
<213> ORGANISM: Artificial Sequence

```
<220> FEATURE:
<223> OTHER INFORMATION: Inhibitory oligonucleotide

<400> SEQUENCE: 8
cctcctcctc ctcctcctcc tcctcctcc                                    29

<210> SEQ ID NO 9
<211> LENGTH: 30
<212> TYPE: DNA
<213> ORGANISM: Artificial Sequence
<220> FEATURE:
<223> OTHER INFORMATION: (CCT)10 inhibitory oligonucleotide

<400> SEQUENCE: 9
cctcctcctc ctcctcctcc tcctcctcct                                   30

<210> SEQ ID NO 10
<211> LENGTH: 31
<212> TYPE: DNA
<213> ORGANISM: Artificial Sequence
<220> FEATURE:
<223> OTHER INFORMATION: (CCT)10C inhibitory oligonucleotide

<400> SEQUENCE: 10
cctcctcctc ctcctcctcc tcctcctcctc                                  31

<210> SEQ ID NO 11
<211> LENGTH: 32
<212> TYPE: DNA
<213> ORGANISM: Artificial Sequence
<220> FEATURE:
<223> OTHER INFORMATION: (CCT)10CC inhibitory oligonucleotide

<400> SEQUENCE: 11
cctcctcctc ctcctcctcc tcctcctcctcc                                 32

<210> SEQ ID NO 12
<211> LENGTH: 33
<212> TYPE: DNA
<213> ORGANISM: Artificial Sequence
<220> FEATURE:
<223> OTHER INFORMATION: (CCT)11 inhibitory oligonucleotide

<400> SEQUENCE: 12
cctcctcctc ctcctcctcc tcctcctcctcct                                33

<210> SEQ ID NO 13
<211> LENGTH: 34
<212> TYPE: DNA
<213> ORGANISM: Artificial Sequence
<220> FEATURE:
<223> OTHER INFORMATION: (CCT)11C inhibitory oligonucleotide

<400> SEQUENCE: 13
cctcctcctc ctcctcctcc tcctcctcctcctc                               34

<210> SEQ ID NO 14
<211> LENGTH: 35
<212> TYPE: DNA
<213> ORGANISM: Artificial Sequence
<220> FEATURE:
<223> OTHER INFORMATION: (CCT)11CC inhibitory oligonucleotide

<400> SEQUENCE: 14
cctcctcctc ctcctcctcc tcctcctcctcctcc                              35
```

```
<210> SEQ ID NO 15
<211> LENGTH: 36
<212> TYPE: DNA
<213> ORGANISM: Artificial Sequence
<220> FEATURE:
<223> OTHER INFORMATION: (CCT)12 inhibitory oligonucleotide

<400> SEQUENCE: 15
cctcctcctc ctcctcctcc tcctcctcctcct                           36

<210> SEQ ID NO 16
<211> LENGTH: 42
<212> TYPE: DNA
<213> ORGANISM: Artificial Sequence
<220> FEATURE:
<223> OTHER INFORMATION: (CCT)14 inhibitory oligonucleotide

<400> SEQUENCE: 16
cctcctcctc ctcctcctcc tcctcctcctcctcctc ct                    42

<210> SEQ ID NO 17
<211> LENGTH: 48
<212> TYPE: DNA
<213> ORGANISM: Artificial Sequence
<220> FEATURE:
<223> OTHER INFORMATION: (CCT)16 inhibitory oligonucleotide

<400> SEQUENCE: 17
cctcctcctc ctcctcctcc tcctcctcctcctcctc ctcctcct              48

<210> SEQ ID NO 18
<211> LENGTH: 18
<212> TYPE: DNA
<213> ORGANISM: Artificial Sequence
<220> FEATURE:
<223> OTHER INFORMATION: (TCC)6 inhibitory oligonucleotide

<400> SEQUENCE: 18
tcctcctcct cctcctcc                                           18

<210> SEQ ID NO 19
<211> LENGTH: 27
<212> TYPE: DNA
<213> ORGANISM: Artificial Sequence
<220> FEATURE:
<223> OTHER INFORMATION: (TCC)9 inhibitory oligonucleotide

<400> SEQUENCE: 19
tcctcctcct cctcctcctc ctcctcc                                 27

<210> SEQ ID NO 20
<211> LENGTH: 36
<212> TYPE: DNA
<213> ORGANISM: Artificial Sequence
<220> FEATURE:
<223> OTHER INFORMATION: (TCC)12 inhibitory oligonucleotide

<400> SEQUENCE: 20
tcctcctcct cctcctcctc ctcctcctcctcctcc                        36

<210> SEQ ID NO 21
<211> LENGTH: 18
<212> TYPE: DNA
<213> ORGANISM: Artificial Sequence
<220> FEATURE:
<223> OTHER INFORMATION: Inhibitory oligonucleotide
```

```
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond

<400> SEQUENCE: 21
cctcctcctc ctcctcct                                                  18

<210> SEQ ID NO 22
<211> LENGTH: 27
<212> TYPE: DNA
<213> ORGANISM: Artificial Sequence
<220> FEATURE:
<223> OTHER INFORMATION: Inhibitory oligonucleotide
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond
<220> FEATURE:
<221> NAME/KEY: modified_base
<222> LOCATION: (19)..(26)
<223> OTHER INFORMATION: phosphorothioate-modified at 3' internucleotide
      bond

<400> SEQUENCE: 22
cctcctcctc ctcctcctcc tcctcct                                        27

<210> SEQ ID NO 23
<211> LENGTH: 27
<212> TYPE: DNA
<213> ORGANISM: Artificial Sequence
<220> FEATURE:
<223> OTHER INFORMATION: Inhibitory oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(26)
<223> OTHER INFORMATION: phosphorothioate-modified at 3' internucleotide
      bond

<400> SEQUENCE: 23
cctcctcctc ctcctcctcc tcctcct                                        27

<210> SEQ ID NO 24
<211> LENGTH: 27
<212> TYPE: DNA
<213> ORGANISM: Artificial Sequence
```

```
<220> FEATURE:
<223> OTHER INFORMATION: Inhibitory oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
<223> OTHER INFORMATION: phosphorothioate-modified at 3' internucleotide
      bond
<220> FEATURE:
<221> NAME/KEY: modified_base
<222> LOCATION: (22)..(26)
<223> OTHER INFORMATION: phosphorothioate-modified at 3' internucleotide
      bond

<400> SEQUENCE: 24
cctcctcctc ctcctcctcc tcctcct                                          27

<210> SEQ ID NO 25
<211> LENGTH: 36
<212> TYPE: DNA
<213> ORGANISM: Artificial Sequence
<220> FEATURE:
<223> OTHER INFORMATION: Inhibitory oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(11)
<223> OTHER INFORMATION: phosphorothioate-modified at 3' internucleotide
      bond
<220> FEATURE:
<221> NAME/KEY: modified_base
<222> LOCATION: (13)..(17)
<223> OTHER INFORMATION: phosphorothioate-modified at 3' internucleotide
      bond
<220> FEATURE:
<221> NAME/KEY: modified_base
<222> LOCATION: (19)..(23)
<223> OTHER INFORMATION: phosphorothioate-modified at 3' internucleotide
      bond
<220> FEATURE:
<221> NAME/KEY: modified_base
<222> LOCATION: (25)..(29)
<223> OTHER INFORMATION: phosphorothioate-modified at 3' internucleotide
      bond
<220> FEATURE:
<221> NAME/KEY: modified_base
<222> LOCATION: (31)..(35)
<223> OTHER INFORMATION: phosphorothioate-modified at 3' internucleotide
      bond

<400> SEQUENCE: 25
cctcctcctc ctcctcctcc tcctcctcctcctcct                                 36

<210> SEQ ID NO 26
<211> LENGTH: 36
<212> TYPE: DNA
<213> ORGANISM: Artificial Sequence
<220> FEATURE:
<223> OTHER INFORMATION: Inhibitory oligonucleotide
<220> FEATURE:
<221> NAME/KEY: modified_base
<222> LOCATION: (1)..(8)
```

```
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond
<220> FEATURE:
<221> NAME/KEY: modified_base
<222> LOCATION: (19)..(26)
<223> OTHER INFORMATION: phosphorothioate-modified at 3' internucleotide
      bond
<220> FEATURE:
<221> NAME/KEY: modified_base
<222> LOCATION: (28)..(35)
<223> OTHER INFORMATION: phosphorothioate-modified at 3' internucleotide
      bond

<400> SEQUENCE: 26
cctcctcctc ctcctcctcc tcctcctcctcctcct                              36

<210> SEQ ID NO 27
<211> LENGTH: 36
<212> TYPE: DNA
<213> ORGANISM: Artificial Sequence
<220> FEATURE:
<223> OTHER INFORMATION: Inhibitory oligonculeotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(32)
<223> OTHER INFORMATION: phosphorothioate-modified at 3' internucleotide
      bond
<220> FEATURE:
<221> NAME/KEY: modified_base
<222> LOCATION: (34)..(35)
<223> OTHER INFORMATION: phosphorothioate-modified at 3' internucleotide
      bond

<400> SEQUENCE: 27
cctcctcctc ctcctcctcc tcctcctcctcctcct                              36

<210> SEQ ID NO 28
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
```

<223> OTHER INFORMATION: phosphorothioate-modified at 3' internucleotide
       bond
<220> FEATURE:
<221> NAME/KEY: modified_base
<222> LOCATION: (22)..(29)
<223> OTHER INFORMATION: phosphorothioate-modified at 3' internucleotide
       bond
<220> FEATURE:
<221> NAME/KEY: modified_base
<222> LOCATION: (31)..(35)
<223> OTHER INFORMATION: phosphorothioate-modified at 3' internucleotide
       bond

<400> SEQUENCE: 28
cctcctcctc ctcctcctcc tcctcctcctcctcct                                   36

<210> SEQ ID NO 29
<211> LENGTH: 18
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
       bond
<220> FEATURE:
<221> NAME/KEY: modified_base
<222> LOCATION: (10)..(17)
<223> OTHER INFORMATION: phosphorothioate-modified at 3' internucleotide
       bond

<400> SEQUENCE: 29
ctcctcctcc tcctcctc                                                      18

<210> SEQ ID NO 30
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
       bond
<220> FEATURE:
<221> NAME/KEY: modified_base
<222> LOCATION: (10)..(17)
<223> OTHER INFORMATION: phosphorothioate-modified at 3' internucleotide
       bond
<220> FEATURE:
<221> NAME/KEY: modified_base
<222> LOCATION: (19)..(26)
<223> OTHER INFORMATION: phosphorothioate-modified at 3' internucleotide
       bond

<400> SEQUENCE: 30
ctcctcctcc tcctcctcct cctcctc                                            27

<210> SEQ ID NO 31
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
       bond
<220> FEATURE:

```
<221> NAME/KEY: modified_base
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(26)
<223> OTHER INFORMATION: phosphorothioate-modified at 3' internucleotide
      bond

<400> SEQUENCE: 31
ctcctcctcc tcctcctcct cctcctc                                              27

<210> SEQ ID NO 32
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
<223> OTHER INFORMATION: phosphorothioate-modified at 3' internucleotide
      bond
<220> FEATURE:
<221> NAME/KEY: modified_base
<222> LOCATION: (22)..(26)
<223> OTHER INFORMATION: phosphorothioate-modified at 3' internucleotide
      bond

<400> SEQUENCE: 32
ctcctcctcc tcctcctcct cctcctc                                              27

<210> SEQ ID NO 33
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond
<220> FEATURE:
<221> NAME/KEY: modified_base
<222> LOCATION: (19)..(26)
<223> OTHER INFORMATION: phosphorothioate-modified at 3' internucleotide
      bond
<220> FEATURE:
<221> NAME/KEY: modified_base
<222> LOCATION: (28)..(35)
<223> OTHER INFORMATION: phosphorothioate-modified at 3' internucleotide
      bond
```

```
<400> SEQUENCE: 33
ctcctcctcc tcctcctcct cctcctcctcctcctc                    36

<210> SEQ ID NO 34
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(32)
<223> OTHER INFORMATION: phosphorothioate-modified at 3' internucleotide
      bond
<220> FEATURE:
<221> NAME/KEY: modified_base
<222> LOCATION: (34)..(35)
<223> OTHER INFORMATION: phosphorothioate-modified at 3' internucleotide
      bond

<400> SEQUENCE: 34
ctcctcctcc tcctcctcct cctcctcctcctcctc                    36

<210> SEQ ID NO 35
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
<223> OTHER INFORMATION: phosphorothioate-modified at 3' internucleotide
      bond
<220> FEATURE:
<221> NAME/KEY: modified_base
<222> LOCATION: (22)..(29)
<223> OTHER INFORMATION: phosphorothioate-modified at 3' internucleotide
      bond
<220> FEATURE:
<221> NAME/KEY: modified_base
<222> LOCATION: (31)..(35)
<223> OTHER INFORMATION: phosphorothioate-modified at 3' internucleotide
      bond

<400> SEQUENCE: 35
ctcctcctcc tcctcctcct cctcctcctcctcctc                    36
```

```
<210> SEQ ID NO 36
<211> LENGTH: 18
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond

<400> SEQUENCE: 36
tcctcctcct cctcctcc                                                   18

<210> SEQ ID NO 37
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond
<220> FEATURE:
<221> NAME/KEY: modified_base
<222> LOCATION: (19)..(26)
<223> OTHER INFORMATION: phosphorothioate-modified at 3' internucleotide
      bond

<400> SEQUENCE: 37
tcctcctcct cctcctcctc ctcctcc                                         27

<210> SEQ ID NO 38
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(26)
<223> OTHER INFORMATION: phosphorothioate-modified at 3' internucleotide
      bond

<400> SEQUENCE: 38
tcctcctcct cctcctcctc ctcctcc                                         27
```

<210> SEQ ID NO 39
<211> LENGTH: 27
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
<223> OTHER INFORMATION: phosphorothioate-modified at 3' internucleotide
      bond
<220> FEATURE:
<221> NAME/KEY: modified_base
<222> LOCATION: (22)..(26)
<223> OTHER INFORMATION: phosphorothioate-modified at 3' internucleotide
      bond

<400> SEQUENCE: 39
tcctcctcct cctcctcctc ctcctcc                                       27

<210> SEQ ID NO 40
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond
<220> FEATURE:
<221> NAME/KEY: modified_base
<222> LOCATION: (19)..(26)
<223> OTHER INFORMATION: phosphorothioate-modified at 3' internucleotide
      bond
<220> FEATURE:
<221> NAME/KEY: modified_base
<222> LOCATION: (28)..(35)
<223> OTHER INFORMATION: phosphorothioate-modified at 3' internucleotide
      bond

<400> SEQUENCE: 40
tcctcctcct cctcctcctc ctcctcctcctcctcc                              36

<210> SEQ ID NO 41
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base

```
<222> LOCATION: (7)..(14)
<223> OTHER INFORMATION: phosphorothioate-modified at 3' internucleotide
      bond
<220> FEATURE:
<221> NAME/KEY: modified_base
<222> LOCATION: (16)..(23)
<223> OTHER INFORMATION: phosphorothioate-modified at 3' internucleotide
      bond
<220> FEATURE:
<221> NAME/KEY: modified_base
<222> LOCATION: (25)..(32)
<223> OTHER INFORMATION: phosphorothioate-modified at 3' internucleotide
      bond
<220> FEATURE:
<221> NAME/KEY: modified_base
<222> LOCATION: (34)..(35)
<223> OTHER INFORMATION: phosphorothioate-modified at 3' internucleotide
      bond

<400> SEQUENCE: 41
tcctcctcct cctcctcctc ctcctcctcctcctcc                                  36

<210> SEQ ID NO 42
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(11)
<223> OTHER INFORMATION: phosphorothioate-modified at 3' internucleotide
      bond
<220> FEATURE:
<221> NAME/KEY: modified_base
<222> LOCATION: (13)..(20)
<223> OTHER INFORMATION: phosphorothioate-modified at 3' internucleotide
      bond
<220> FEATURE:
<221> NAME/KEY: modified_base
<222> LOCATION: (22)..(29)
<223> OTHER INFORMATION: phosphorothioate-modified at 3' internucleotide
      bond
<220> FEATURE:
<221> NAME/KEY: modified_base
<222> LOCATION: (31)..(35)
<223> OTHER INFORMATION: phosphorothioate-modified at 3' internucleotide
      bond

<400> SEQUENCE: 42
tcctcctcct cctcctcctc ctcctcctcctcctcc                                  36

<210> SEQ ID NO 43
<211> LENGTH: 22
<212> TYPE: DNA
<213> ORGANISM: Artificial Sequence
<220> FEATURE:
<223> OTHER INFORMATION: CpG2395 TLR9 stimulatory oligonucleotide
<220> FEATURE:
<221> NAME/KEY: modified_base
<222> LOCATION: (1)..(21)
<223> OTHER INFORMATION: phosphorothioate-modified at 3' internucleotide
      bond

<400> SEQUENCE: 43
tcgtcgtttt cggcgcgcgc cg                                                22

<210> SEQ ID NO 44
```

```
<211> LENGTH: 20
<212> TYPE: DNA
<213> ORGANISM: Artificial Sequence
<220> FEATURE:
<223> OTHER INFORMATION: CpG2216 stimulatory oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (15)..(19)
<223> OTHER INFORMATION: phosphorothioate-modified at 3' internucleotide
      bond

<400> SEQUENCE: 44
gggggacgat cgtcggggggg                                            20

<210> SEQ ID NO 45
<211> LENGTH: 18
<212> TYPE: DNA
<213> ORGANISM: Artificial Sequence
<220> FEATURE:
<223> OTHER INFORMATION: Inhibitory oligonucleotide
<220> FEATURE:
<221> NAME/KEY: modified_base
<222> LOCATION: (1)..(17)
<223> OTHER INFORMATION: phosphorothioate-modified at 3' internucleotide
      bond

<400> SEQUENCE: 45
cctcctcctc ctcctcct                                               18

<210> SEQ ID NO 46
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(35)
<223> OTHER INFORMATION: phosphorothioate-modified at 3' internucleotide
      bond

<400> SEQUENCE: 46
cctcctcctc ctcctcctcc tcctcctcctcctcct                            36

<210> SEQ ID NO 47
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(17)
<223> OTHER INFORMATION: phosphorothioate-modified at 3' internucleotide
      bond
<220> FEATURE:
<221> NAME/KEY: modified_base
<222> LOCATION: (19)..(29)
<223> OTHER INFORMATION: phosphorothioate-modified at 3' internucleotide
      bond
<220> FEATURE:
<221> NAME/KEY: modified_base
<222> LOCATION: (31)..(35)
```

```
<223> OTHER INFORMATION: phosphorothioate-modified at 3' internucleotide
      bond

<400> SEQUENCE: 47
cctcctcctc ctcctcctcc tcctcctcctcctcct                                    36

<210> SEQ ID NO 48
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
<221> NAME/KEY: modified_base
<222> LOCATION: (4)..(8)
<223> OTHER INFORMATION: phosphorothioate-modified at 3' internucleotide
      bond
<220> FEATURE:
<221> NAME/KEY: modified_base
<222> LOCATION: (10)..(20)
<223> OTHER INFORMATION: phosphorothioate-modified at 3' internucleotide
      bond
<220> FEATURE:
<221> NAME/KEY: modified_base
<222> LOCATION: (22)..(32)
<223> OTHER INFORMATION: phosphorothioate-modified at 3' internucleotide
      bond
<220> FEATURE:
<221> NAME/KEY: modified_base
<222> LOCATION: (34)..(35)
<223> OTHER INFORMATION: phosphorothioate-modified at 3' internucleotide
      bond

<400> SEQUENCE: 48
cctcctcctc ctcctcctcc tcctcctcctcctcct                                    36

<210> SEQ ID NO 49
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(35)
<223> OTHER INFORMATION: phosphorothioate-modified at 3' internucleotide
      bond

<400> SEQUENCE: 49
tcctcctcct cctcctcctc ctcctcctcctcctcc                                    36

<210> SEQ ID NO 50
<211> LENGTH: 36
<212> TYPE: DNA
<213> ORGANISM: Artificial Sequence
<220> FEATURE:
<223> OTHER INFORMATION: Inhibitory Oligonucleotide
<220> FEATURE:
<221> NAME/KEY: modified_base
<222> LOCATION: (1)..(5)
<223> OTHER INFORMATION: phosphorothioate-modified at 3' internucleotide
      bond
<220> FEATURE:
<221> NAME/KEY: modified_base
<222> LOCATION: (7)..(17)
<223> OTHER INFORMATION: phosphorothioate-modified at 3' internucleotide
      bond
<220> FEATURE:
```

```
<221> NAME/KEY: modified_base
<222> LOCATION: (19)..(29)
<223> OTHER INFORMATION: phosphorothioate-modified at 3' internucleotide
      bond
<220> FEATURE:
<221> NAME/KEY: modified_base
<222> LOCATION: (31)..(35)
<223> OTHER INFORMATION: phosphorothioate-modified at 3' internucleotide
      bond

<400> SEQUENCE: 50
tcctcctcct cctcctcctc ctcctcctcctcctcc                              36
```

TLR INHIBITORY OLIGONUCLEOTIDES AND THEIR USE

TECHNICAL FIELD

The present invention relates to the oligonucleotides and remedies using the oligonucleotides for treating immune-mediated disorders. The immune-mediated disorder includes autoimmune disease, graft rejection, hypersensitivity, disease associated with the over-stimulation of host's immune system by autoantigens, microbes, Toll-like receptor (TLR)-mediated disease, NF-kB-mediated disease, interferon-mediated disease, and inflammatory cytokine-mediated inflammatory disease.

BACKGROUND ART

The immune system protects human body from bacterial, parasitic, fungal, viral infections and from the growth of tumor cells. Immunity can be classified as innate immunity and adaptive immunity. Innate immune responses typically occur immediately upon infection for providing of an early barrier to infectious disease whereas adaptive immune responses occur later with the generation of antigen-specific long term protective immunity.

However, the unwanted immune response can sometimes occur, which may result in immune-mediated disorders. The disorders include autoimmune diseases, graft rejection, hypersensitivity, diseases associated with the over-stimulation of host's immune system by microbes, Toll-like receptor (TLR)-mediated diseases, interferon-mediated diseases, NF-kB-mediated diseases and inflammatory cytokine-mediated inflammatory diseases. An autoimmune disease results from adaptive immune responses, innate immune responses or both against endogenous and/or exogenous antigens. Foreign substances, derived from bacteria, parasites, fungi or viruses, may mimic self-proteins and stimulate the immune system to launch responses to a self-cell and tissue, resulting in the diseases including but not limited to systemic lupus erythematosus (SLE) and rheumatoid arthritis. The graft rejection is a consequence of organ or tissue transplantation caused by the immune response in the transplant recipient (host) to the transplanted organ/tissue. When a subject is transplanted with grafts including kidney, pancreas, heart, lung, bone marrow, cornea and skin, the subject can launch an immune response (rejection) against the grafts. Hypersensitivity is an inappropriate immune response that has deleterious effects, resulting in significant tissue damage or even death. The hypersensitivity is divided into four types (e.g. Types I, II, III and IV). Disease associated with the over-stimulation of host's immune system by microbes is triggered by the infection of viruses such as flu viruses and other microbes. In the case of flu virus and Gram-negative bacterial infection, an excessive immune response to the invaders appears to be a fatal factor in patients. The response is characterized by the overproduction of cytokines. Studies of septic shock syndrome demonstrate that over-production/aberrant production of cytokines can lead to rapid mortality due to cytokine-mediated lethal shock (Slifka et al., J Mol Med. 2000, 78, 74-80). Septic shock following gram-negative infection is a leading cause of mortality in critically ill patients. The exaggerated production of cytokines is known to contribute to sepsis characterized by cytokine-mediated lethal shock (Espat et al., J Surg Res, 1995, 59, 153-8). Multiple organ dysfunction syndromes (MODS) are a major cause of morbidity and mortality in severe sepsis and shock. Cytokine-mediated lethal shock resulted from over-production of host cytokines is considered as a main mechanism leading to MODS (Wang et al., Am J Emerg Med, 2008, 26, 711-5). Toll-like receptor (TLR)-mediated disease is a disorder caused by the activation of Toll like receptors (TLRs).

TLRs are a family of receptors that recognize microbe derived molecular structures (pathogen-associated molecular patterns or PAMPs). TLR expressing immune cells are activated upon binding of PAMPs. TLRs recognize a range of pathogen-derived products and are activated. Lipopolysaccharide (LPS) of bacteria is recognized by TLR4; lipoteichoic acid and diacylated lipopeptides, by TLR2-TLR6 dimer; triacylated lipopeptides, by TLR2-TLR1 dimer; CpG containing oligonucleotide (CpG ODN) synthesized or derived from either viruses or bacteria, by TLR9; bacterial flagellin, by TLR5; zymosan, by TLR2-TLR6 dimer; F protein from respiratory syncytial virus (RSV), by TLR4; viral-derived double-stranded RNA (dsRNA) and poly I:C, a synthetic analogue of dsRNA, by TLR3; viral DNA, by TLR9; single-stranded viral RNA (VSV and flu virus) and synthetic guanosine analogues such as imidazoquinolines and imiquimod, by TLR7 and TLR8 (Liew et al., Nature Reviews Immunology, 2005, 5, 446-458).

In recent years, TLR activation has been connected to the pathogenesis of some of diseases including sepsis, dilated cardiomyopathy, diabetes, experimental autoimmune encephalomyelitis, systemic lupus erythematosus, atherosclerosis, asthma, chronic obstructive pulmonary disease and organ failure (Liew et al., Nature Review Immunology, 2005, 5, 446-458). Activation of TLR9 by self DNA plays an important role in the development of autoimmune diseases such as psoriasis (Gilliet et al., Nat. Rev. Immunol. 2008, 8, 594-606), SLE (Christensen et al., Immunity, 2006, 25, 417-28; Barrat, et al., J Exp Med, 2005, 202, 1131-9; Wellmann, et al., Proc Natl Acad Sci USA, 2005, 102, 9258-63) and rheumatoid arthritis (Leadbetter et al., Nature, 2002, 416, 603-7; Boule et al., J Exp Med, 2004, 199, 1631-40). It was also documented that TLR9 agonist activates both innate and adaptive immune response (Krieg, Nature Reviews Drug Discovery, 2006, 5, 471-484).

It was reported that an oligonucleotide with a nucleotide sequence of 5'-cctcctcctcctcctcctcctcct-3' (SEQ ID NO:3) prevented proliferation of human peripheral blood mononuclear cells (PBMCs) and production of interferons (IFNs), which is induced by TLR9 agonist (U.S. Pat. No. 8,030,289B2). It was also documented that oligonucleotide revealed by a nucleotide sequence (CCT)nCm, wherein the n is an integer from 2 to 50 and the m is 0, 1, or 2, possesses TLR7, 8 and 9 inhibition property with suppression of NF-kB dependent immune response and production of inflammatory cytokines, such as IFNa and Tumor Necrosis Factor alpha (TNFa) (EP2154144, WO2014/082254), which implies the broad use of the oligonucleotide (CCT)nCm for the treatment of immune-mediated disorders.

The oligonucleotides with plain phosphodiester bonding in the backbone normally have been reported for its susceptibility to nucleases in vivo, such as serum exonucleases or intracellular endonucleases (Stein et al., Nuc Acid Res, 1988, 16, 3209-3221), resulting in poor profiles of pharmacokinetics. To solve such problems, there have been some strategies taken such as to modify backbones with nuclease-resistant structures including phosphorothioation. Meanwhile, phosphorothioation has notoriously been described for having strong liver and kidney toxicity (Henry et al., Toxicol Pathol, 1999, 28, 95-100; Monteith et al., Toxicol Pathol, 1999, 27, 307-317), which impedes the use of the phosphorothioated oligonucleotides for the treatment of systemic diseases. Thus some trials have been made to decrease the toxicity, such as the change in the nucleotide sequences (Hagedorn et al., Nuc Acid Ther, 2013, 23, 302-310, Burdick et al., Nuc Acid Res, 2014, 42, 4882-4891). However, regarding the oligonucleotides in this invention, described as CxTy(CCT)nCm, the above-mentioned strategy to change nucleotide sequences could not have been made, as the efficacy of the oligonucleotides solely depends on the unique nucleotide sequence.

CITATION LIST

Patent Literature

[PTL 1]
U.S. Pat. No. 8,030,289B2
[PTL 2]
EP2154144
[PTL 3]
WO2014/082254
[PTL 4]
JP5011520

Non Patent Literature

[NPL 1]
Slifka et al., J Mol Med. 2000, 78, 74-80
[NPL 2]
Espat et al., J Surg Res, 1995, 59, 153-8
[NPL 3]
Wang et al., Am J Emerg Med, 2008, 26, 711-5
[NPL 4]
Liew et al., Nature Reviews Immunology, 2005, 5, 446-458
[NPL 5]
Gilliet et al., Nat. Rev. Immunol. 2008, 8, 594-606
[NPL 6]
Christensen et al., Immunity, 2006, 25, 417-28
[NPL 7]
Barrat, et al., J Exp Med, 2005, 202, 1131-9
[NPL 8]
Wellmann, et al., Proc Natl Acad Sci USA, 2005, 102, 9258-63
[NPL 9]
Leadbetter et al., Nature, 2002, 416, 603-7
[NPL 10]
Boule et al., J Exp Med, 2004, 199, 1631-40
[NPL 11]
Krieg, Nature Reviews Drug Discovery, 2006, 5, 471-484
[NPL 12]
Stein et al., Nuc Acid Res, 1988, 16, 3209-3221
[NPL 13]
Henry et al., Toxicol Pathol, 1999, 28, 95-100
[NPL 14]
Monteith et al., Toxicol Pathol, 1999, 27, 307-317
[NPL 15]
Hagedorn et al., Nuc Acid Ther, 2013, 23, 302-310
[NPL 16]
Burdick et al., Nuc Acid Res, 2014, 42, 4882-4891
[NPL 17]
Klinman, Nat. Rev. Immunol, 2004, 4, 249-258
[NPL 18]
Marshall et al., Infect Immun, 1998, 66, 1325-33
[NPL 19]
Peter et al., Immunology, 2008, 123, 118-28
[NPL 20]
The Gilmore Lab, Boston University Biology [online, retrieved on Nov. 4, 2015] Retrieved from Internet: <URL: http://www.bu.edu/nf-kb/physiological-mediators/diseases/>
[NPL 21]
Tak et al., J Clin Invest, 2001, 107, 7-11
[NPL 22]
Baldwin (Jr) et al., Annu Rev Immunol, 1996, 14, 649-683
[NPL 23]
Miyazawa et al., Am J Pathol 1998, 152, 793-803
[NPL 24]
Schottelius et al., J Biol Chem 1999, 274, 31868-31874
[NPL 25]
Neurath et al., Ann NY Acad Sci, 1998, 859, 149-159
[NPL 26]
Liu et al., Neurosci Bull, 2012, 28, 131-44
[NPL 27]
Liu et al., Itch: Mechanisms and Treatment, Carstens E, Akiyama T, editors, 2014, CRC Press/Taylor & Francis
[NPL 28]
Sun et al., Clin Immunol, 2010, 134, 262-276
[NPL 29]
Zhang et al., International Immunopharmacol, 2012, 446-453
[NPL 30]
Freier et al., Nuc Acid Res, 1997, 25, 4429-4443
[NPL 31]
Kuwahara et al., Molecules, 2010, 15, 5423-5444
[NPL 32]
Deleavey et al., Chemistry & Biology, 19, 937-954
[NPL 33]
Mutisya et al., Nucleic Acids Research, 2014, 42, 6542-6551
[NPL 34]
Sharma et al., Med. Chem. Commun. 2014, 5, 1454-1471
[NPL 35]
Davidson, Engl J Med, 2001, 345, 340-350
[NPL 36]
Delgado-Vega et al., Arthritis Research & Therapy 2010, 12/S2
[NPL 37]
Goldsby et al., Immunology, Fifth Edition, 2003, W.H. FREEMAN AND COMPANY
[NPL 38]
The Writing Committee of the World Health Organization (WHO) Consultation on Human Influenza A/H5, N Engl J Med, 2005, 353, 1374-85
[NPL 39]
Patel et al., Mol Cell Neurosci, 2014, 63, 38-48
[NPL 40]
Smith, Curr Opin Nehrol Hypertens, 2009, 18, 189
[NPL 41]
Gambuzza et al., J Neuroimmunol, 2011, 239, 1-12
[NPL 42]
Hatemi et al., Clin Exp Rheumatol, 2015, 33 (6 Suppl 94), 3-14
[NPL 43]
Tang et al., Respirology, 2015, October 18. doi: 10.1111/resp.12657. [Epub ahead of print]
[NPL 44]
Ito et al., Blood, 2006, 107, 2423-2431
[NPL 45]
Guidance for Industry, Estimating the Maximum Safe Starting Dose in Initial Clinical Trials for Therapeutics in Adult Healthy Volunteers, U.S. Department of Health and Human Services Food and Drug Administration, Center for Drug Evaluation and Research (CDER), July 2005

[NPL 46]
Maeda et al., Int J Hematol., 2005, 81, 148-54

SUMMARY OF INVENTION

Technical Problem

This present invention is intended to provide safer pharmaceutical composition and to allow increased dosing regimen of the said pharmaceutical composition with increased efficacy against the targeted diseases.

The present invention provides an oligonucleotide without toxicity. The oligonucleotide of the invention comprises an oligonucleotide stretch with a formula of CxTy(CCT)nCm, which is partially phosphorothioated by replacing one or more non-bridging oxygen with sulfur atom in the internucleotide linkage, wherein the n is an integer from 2 to 50, or preferably 5-16, x denotes integer 0 or 1, y denotes integer 0 (only when x=0) or 1 (x can either be 0 or 1), and the m is 0, 1, or 2.

In this invention, the inventors identified that some oligonucleotides with partial phosphorothioation achieved reduction of toxicity along with the maintenance of stability in serum, which enables safer formulation of the pharmaceutical compositions; at the same time, the safe profiles of the oligonucleotides allow to increase the dosing levels of the each of the said oligonucleotide, which will lead to the increased efficacy for the treatment of targeted diseases in the human or non-human animals receiving the treatment.

BRIEF DESCRIPTION OF DRAWINGS

[FIG. 1]

FIG. 1a shows the stability of partially phosphorothioated (CCT)12 oligonucleotide species in the serum-containing medium. The oligonucleotides were incubated in the medium supplemented with serum and the remaining oligonucleotides in the medium were quantified. As shown in the figure, the CCT12PO with normal phosphodiester internucleotide bonds showed almost complete degradation after 1-day incubation, while fully phosphorothioated CCT12PS showed longer duration, which reveals the fast degradation of the oligonucleotide without internucleotide modification. Meanwhile, partially phosphorothioated CCT12-3 (see details for the EXAMPLES section) shows comparable stability with CCT12PS, which reveals that at least certain levels of phosphorothioation at internucleotide linkages will be enough to achieve stability against nucleases in serum. FIG. 1b shows the stability of partially phosphorothioated (TCC)12 oligonucleotide species in the serum-containing medium. It was shown that while the oligonucleotide without phosphorothioation (TCC12PO) showed rapid degradation after 1-day incubation, while the partially phosphorothioated oligonucleotide (TCC12-6) revealed increased stability as much as the fully phosphorothioated species with the same sequence (TCC12PS).

FIG. 2 reveals the decrease in toxicity of the oligonucleotides by the reduced phosphorothioation levels with certain patterns. FIG. 2a shows the decrease in toxicity of (CCT)12 by the reduction of phosphorothioation levels. As shown here, CCT12-1 did not show apparent body weight reduction even though the oligonucleotide CCT12PS with the same sequence showed strong toxicity as in the case of another fully phosphorothioated oligonucleotide CCT8PS. FIG. 2b shows the comparison of the oligonucleotides between CCT12-2, CCT12-3, CCT12-4, and CCT12-5, which implies that the reduction of toxicity was not just achieved by the reduction of phosphorothioation levels but rather has relationship with the phosphorothioation patterns.

FIG. 2c shows that the reduction of toxicity by the change in phosphorothioation patterns is also applicable to (TCC) repeats. TCC12-6 showed reduction in the toxicity, while TCC12-7, which has same levels of phosphorothioation still possessed significant toxicity. FIGS. 2d and 2e shows the increase in ALT also occurred by the oligonucleotide which showed strong toxicity.

FIG. 3a shows the inhibitory effect of partially phosphorothioated oligonucleotide on NF-kB transcriptional activity. Although CCT12-1, CCT12-2, and CCT12-3 showed reduced toxicity, they still conserve the inhibitory activity. FIGS. 3b and c reveals that the reduction in the toxicity by the change in phosphorothioation pattern does not affect the inhibitory activity of the oligonucleotides, such shown by the oligonucleotides, CCT12-3 and TCC12-6.

FIGS. 4a, b, and c shows graphs depicting the suppression ability of inhibitory-oligonucleotides on TNFa and interleukin (IL)-6 productions from CAL-1 cells stimulated with TLR7/8 agonist, Gardiquimod or TLR9 agonist, CpG2395. The change in phosphorothioation pattern to decrease toxicity does not have significant effect on the inhibitory effect against TLR7, 8 or TLR9 activation.

FIGS. 5a and b show graphs depicting the suppression activity of inhibitory-oligonucleotides on IFNa production from human PBMC stimulated with CpG2216. These graphs (5a and 5b) also reveal that the change in phosphorothioation patterns does not significantly affect inhibitory activity of the oligonucleotides against IFNa production levels induced by TLR9 agonist.

DETAILED DESCRIPTION

The present invention provides a pharmaceutical composition containing an oligonucleotide or oligonucleotides that comprises an oligonucleotide with a formula of CxTy(CCT)nCm, wherein the n is an integer from 2 to 50, or preferably 5-16, x denotes integer 0 or 1, y denotes integer 0 (only when x=0) or 1 (x can either be 0 or 1), and the m is either 0, 1, or 2. The examples of the sequences of oligonucleotides are as following:

```
                                          (SEQ ID NO: 1)
   5'-cctcctcctcctcctcct-3'.

(SEQ ID NO: 2)
   5'-cctcctcctcctcctcctcct-3'.

(SEQ ID NO: 3)
   5'-cctcctcctcctcctcctcctcct-3'.

(SEQ ID NO: 4)
   5'-cctcctcctcctcctcctcctcctc-3'.

(SEQ ID NO: 5)
   5'-cctcctcctcctcctcctcctcctcc-3'.

(SEQ ID NO: 6)
   5'-cctcctcctcctcctcctcctcctcct-3'.

(SEQ ID NO: 7)
   5'-cctcctcctcctcctcctcctcctcctc-3'.

(SEQ ID NO: 8)
   5'-cctcctcctcctcctcctcctcctcctcc-3'.

(SEQ ID NO: 9)
   5'-cctcctcctcctcctcctcctcctcctcct-3'.
```

(SEQ ID NO: 10)
5'-cctcctcctcctcctcctcctcctcctcctc-3'.

(SEQ ID NO: 11)
5'-cctcctcctcctcctcctcctcctcctcctcc-3'.

(SEQ ID NO: 12)
5'-cctcctcctcctcctcctcctcctcctcctcct-3'.

(SEQ ID NO: 13)
5'-cctcctcctcctcctcctcctcctcctcctcctc-3'.

(SEQ ID NO: 14)
5'-cctcctcctcctcctcctcctcctcctcctcctcc-3'.

(SEQ ID NO: 15)
5'-cctcctcctcctcctcctcctcctcctcctcctcct-3'.

(SEQ ID NO: 16)
5'-cctcctcctcctcctcctcctcctcctcctcctcctcct-3'.

(SEQ ID NO: 17)
5'-cctcctcctcctcctcctcctcctcctcctcctcctcctcctcct-3'.

(SEQ ID NO: 18)
5'-tcctcctcctcctcc-3'.

(SEQ ID NO: 19)
5'-tcctcctcctcctcctcctcctcc-3'.

(SEQ ID NO: 20)
5'-tcctcctcctcctcctcctcctcctcctcctcc-3'.

wherein the oligonucleotide of the invention can be screened based on the reduced toxicity compared to the fully phosphorothioated oligonucleotides with the same sequence, by the arrangement of the pattern of chemical modification in the internucleotide bonds; the chemical modification is optionally phosphorothioation.

Preferably, the present invention provides oligodeoxynucleotides with partial phosphorothioation which replaces non-bridging O atoms with S with certain pattern, resulting in maintenance of the activity of oligonucleotides and stability in vivo, while leads to the least levels of toxicity when administered to animals. The example of the said oligodeoxynucleotides of the present invention with reduced toxicity comprises stretches of fully phosphorothioated CCTCCTCCT, CTCCTCCTC or TCCTCCTCC, or their truncated derivatives, connected by normal phosphodiester bonds. The said oligonucleotide includes following:

(SEQ ID NO.: 21)
5'-CCTCCTCCtCCTCCTCCt-3', (SEQ ID NO.: 22)
5'-CCTCCTCCtCCTCCTCCtCCTCCTCCt-3', (SEQ ID NO.: 23)
5'-CCTCCtCCTCCTCCtCCTCCTCCtCCt-3', (SEQ ID NO.: 24)
5'-CCtCCTCCTCCtCCTCCTCCtCCTCCt-3', (SEQ ID NO.: 25)
5'-CCTCCtCCTCCtCCTCCtCCTCCtCCTCCtCCTCCt-3'

(SEQ ID NO.: 26)
5'-CCTCCTCCtCCTCCTCCtCCTCCTCCtCCTCCTCCt-3', (SEQ ID NO.: 27)
5'-CCTCCtCCTCCTCCtCCTCCTCCtCCTCCTCCtCCt-3'

(SEQ ID NO.: 28)
5'-CCtCCTCCTCCtCCTCCTCCtCCTCCTCCtCCTCCt-3', (SEQ ID NO.: 29)
5'-CTCCTCCTcCTCCTCCTc-3', (SEQ ID NO.: 30)
5'-CTCCTCCTcCTCCTCCTcCTCCTCCTc-3', (SEQ ID NO.: 31)
5'-CTCCTcCTCCTCCTcCTCCTCCTcCTc-3', (SEQ ID NO.: 32)
5'-CTcCTCCTCCTcCTCCTCCTcCTCCTc-3', (SEQ ID NO.: 33)
5'-CTCCTCCTcCTCCTCCTcCTCCTCCTcCTCCTCCTc-3', (SEQ ID NO.: 34)
5'-CTCCTcCTCCTCCTcCTCCTCCTcCTCCTCCTcCTc-3', (SEQ ID NO.: 35)
5'-CTcCTCCTCCTcCTCCTCCTcCTCCTCCTcCTCCTc-3', (SEQ ID NO.: 36)
5'-TCCTCCTCcTCCTCCTCc-3', (SEQ ID NO.: 37)
5'-TCCTCCTCcTCCTCCTCcTCCTCCTCc-3', (SEQ ID NO.: 38)
5'-TCCTCcTCCTCCTCcTCCTCCTCcTCc-3', (SEQ ID NO.: 39)
5'-TCcTCCTCCTCcTCCTCCTCcTCCTCc-3', (SEQ ID NO.: 40)
5'-TCCTCCTCcTCCTCCTCcTCCTCCTCcTCCTCCTCc-3', (SEQ ID NO.: 41)
5'-TCCTCcTCCTCCTCcTCCTCCTCcTCCTCCTCcTCc-3', (SEQ ID NO.: 42)
5'-TCcTCCTCCTCcTCCTCCTCcTCCTCCTCcTCCTCc-3', wherein the capital case letter denotes the base is phosphorothioate-modified in the internucleotide linkage at 3', and the lower case letter denotes that the bases the base is un-modified. The common structural feature of the oligonucleotides, which comprising stretches of fully phosphorothioated CCTCCTCCT, CTCCTCCTC or TCCTCCTCC, or their truncated derivatives, connected by the normal phosphodiester bonds, allows the reduction of the toxicity shown by the fully phosphorothioated oligonucleotides with the structure formulated as CxTy(CCT)nCm, wherein the n is an integer from 2 to 50, or preferably 5-16, x denotes integer 0 or 1, y denotes integer 0 (only when x=0) or 1 (x can either be 0 or 1), and the m is either 0, 1, or 2.

The oligonucleotide of the present invention strongly inhibits TLR9 activation. CpG containing oligonucleotides (CpG ODN) is known as a TLR9 agonist (Klinman, Nat. Rev. Immunol, 2004, 4, 249-258). The oligonucleotide of the invention strongly inhibits the cytokines stimulated by CpG ODN, indicating that the oligonucleotides of the invention can be used as a remedy for the treatment of diseases related to TLR9 over-activation or other diseases which can be treated by the suppression of TLR9 signaling. For example, because TLR9 activation has been reported to contribute to the development of psoriasis (Gilliet et al., Nat. Rev. Immunol., 2008, 8, 594-606), SLE (Barrat et al., J Exp Med, 2005, 202, 1131-9; Wellmann et al., Proc Natl Acad Sci USA, 2005, 102, 9258-63; Christensen et al., Immunity, 2006, 25, 417-28) and rheumatoid arthritis (Leadbetter et al., Nature, 2002, 416, 603-7; Boule et al, J Exp Med, 2004, 199, 1631-40), the oligonucleotide of the invention can be used as a remedy for the treatment of psoriasis, SLE and rheumatoid arthritis by inhibiting the TLR9 activation.

The oligonucleotide of the present invention strongly inhibits IFN production from human PBMC induced by TLR9 agonist. Thus the present invention can treat disease associated with IFNa over-production or the diseases treated by the suppression of IFNa production. For example, because the elevated production of IFNs contribute to the development of SLE, as has been reported (Barrat et al., J Exp Med, 2005, 202, 1131-9; Wellmann et al., Proc Natl Acad Sci USA, 2005, 102, 9258-63), the oligonucleotides of the invention can be used as a remedy for the treatment of SLE by inhibiting IFN production.

It has been demonstrated that injection of TLR9 agonist; CpG ODN with the D-galactosamine (D-Gal) into mice induced hyper immune reactions. The model mice died within 12 to 24 h. Analyses of plasma cytokines revealed over-production of proinflammatory cytokines such as TNFa (Marshall et al., Infect Immun, 1998, 66, 1325-33; Peter et al., Immunology, 2008, 123, 118-28). The oligonucleotide of the present invention strongly inhibits the production of TNFa from mouse cells induced by TLR9 stimulation. Because the cytokine-mediated lethal shock contributes to the septic shock (Slifka et al., J Mol Med, 2000, 78, 74-80; Espat et al., J Surg Res, 1995, 59, 153-8) and multiple organ dysfunction syndromes (MODS) (Wang et al., Am J Emerg Med, 2008, 26, 711-5), the oligonucleotides of the present invention can be used as a remedy for the treatment of sepsis and MOGS by rescuing the host from cytokine-mediated lethal shock.

The oligonucleotide of the present invention also strongly inhibits the cytokine production which is induced by TLR7 or TLR8 agonist. The oligonucleotides of the present invention can be used as a remedy for the treatment of Toll-like receptor (TLR)-mediated disease by inhibiting TLR7 or TLR8.

The oligonucleotides of the invention strongly inhibit NF-kB activation induced by TLR stimulation, indicating that the oligonucleotides of the invention can be used as a remedy for the treatment of diseases related to NF-kB activation. As NF-kB activation has been reported to contribute to the development of various diseases (http://www.bu.edu/nf-kb/physiological-mediators/diseases/; Tak et al., J Clin Invest, 2001, 107, 7-11), the oligonucleotides of the invention can be used as a remedy for the treatment of symptoms which occur in such diseases by inhibiting the NF-kB activation. In some cancers, overactivation of NF-kB is reported and inhibitory function of the present invention may be used also for treating such cancers.

NF-kB is one of the most important regulators of proinflammatory gene expression. Activation of the NF-kB plays a central role in inflammation through its ability to induce transcription of proinflammatory cytokines (Baldwin (Jr) et al., Annu Rev Immunol, 1996, 14, 649-683). It has been demonstrated that NF-kB plays a role in constitutive IL-6 production in rheumatoid arthritis (RA) synovial fibroblasts (Miyazawa et al., Am J Pathol 1998, 152, 793-803). NF-kB is also involved in activation of inflammatory genes by IL-1 or TNFα in human monocytes (Schottelius et al., J Biol Chem 1999, 274, 31868-31874). The number of NF-kB positive cells correlates with the degree of gastritis. Similarly, there is evidence of NF-kB activation in inflammatory bowel disease, where lamina propria macrophages display activated NF-kB (Neurath et al., Ann NY Acad Sci, 1998, 859, 149-159).

The activation of TLRs by the ligands induces the activation of transcription factors such as NF-kB and interferon responsive factors (IRFs). Those activated transcription factors further induce the production of inflammatory cytokines such as IL-6, IL-1, IL-8, TNFa and the IFNs. Production of inflammatory cytokines can cause diseases such as, but not limited to, autoimmune diseases, allergies, and hypersensitivity, therefore the present invention is expected for the treatment of such diseases with inflammation.

Inflammatory cytokine, such as TNFa, IFNs, IL-1, IL-6 and IL-12, also activates downstream prostaglandin production, which is involved in the pain formation under disease condition. TLRs also were reported to be expressed in the CNSs and PNSs, which is involved in the pain sensing (Liu et al., Neurosci Bull, 2012, 28, 131-44; Liu et al., Itch: Mechanisms and Treatment, Carstens E, Akiyama T, editors, 2014, CRC Press/Taylor & Francis). Thus the present invention is expected for the use in the cure of such pain symptoms caused by the inflammatory conditions.

As it can be understood from the above notions on the functions of the present invention, the present invention provides a remedy for treating immune-mediated disorder by administering the oligonucleotides of the invention alone or with a pharmaceutically acceptable carrier to a subject; the administration can be enteral, parenteral, subcutaneous, intravenous, transdermal, sublingual, intranasal, transmucosal, pulmonary, oral, gastric, intestinal, rectal, vaginal, aerosol, intraocular, intratracheal, intrarectal, intraspinal, intramuscular, intraarticular, intraperitoneal, intracardiac, intraosseus, intrathecal, intravitreal, inhalational or topical.

In another embodiment, the present invention provides a remedy for the treatment of immune-mediated disorder by administering the oligonucleotides of the invention alone or in combination with additional active ingredients.

In another embodiment, the present invention provides a remedy for the treatment of immune-mediated disorder by administering the oligonucleotides of the invention in delivery vehicles.

In another embodiment, the oligonucleotide of the present invention is modified with the linking of one or more polyethylene glycol (PEG) chains. The PEGylated oligonucleotide can prolong the circulation time in vivo by reducing renal clearance.

As indicated above, the present invention provides methods to regulate an immune response in an individual, comprising administering to an individual immunostimulatory compounds in an amount sufficient to regulate an immune response in said individual. Immunoregulation according to the methods of this invention may be practiced on individuals including those suffering from a disorder associated with an unwanted activation of immune response.

In another embodiment, the present invention provides a remedy for treating immune-mediated disorder using the oligonucleotides of the invention. The immune-mediated disorder includes autoimmune disease, graft rejection, hypersensitivity, diseases associated with the over-stimulation by of host's immune system by autoantigens, microbes and Toll-like receptor (TLR)-mediated disease.

In another embodiment, the present invention provides a remedy for treating Toll-like receptor (TLR)-mediated diseases, TLR9-mediated diseases, TLR7 and/or 8-mediated diseases, Hypersensitivity, Diseases associated with the over-stimulation of host's immune system by microbes, Graft rejection, Interferon-mediated diseases and inflammatory cytokine-mediated inflammation diseases using the oligonucleotides of the invention by inhibiting the TLR activation and inflammatory cytokine production induced by TLR antagonists such as viruses or the self-antigen in autoimmune patients.

In another embodiment, the present invention provides methods of regulating a TLR9 dependent immune response in an individual in an amount sufficient to prevent TLR9 dependent cytokine production in said individual, comprising co-administering to an individual with immunostimulatory compounds.

In another embodiment, the present invention provides methods of regulating a TLR7 and/or TLR8 dependent immune response in an individual in an amount sufficient to prevent TLR7 and/or TLR8 dependent cytokine production in said individual, comprising co-administering to an individual with immunostimulatory compounds.

In another embodiment, the present invention provides a remedy for treating immune-mediated diseases using the oligonucleotides of the invention by inhibiting production of proinflammatory cytokines to rescue a subject from diseases such as inflammation or cytokine-mediated lethal shock.

In another embodiment, the present invention provides methods of regulating a NF-kB dependent immune response in an individual in an amount sufficient to prevent NF-kB dependent cytokine production in said individual, comprising co-administering to an individual with immunostimulatory compounds.

In another embodiment, the present invention provides a remedy for treating immune-mediated disorders using the oligonucleotides of the invention by inhibiting NF-kB activation induced by TLR stimulation.

In another embodiment, the present invention majorly inhibits activation of TLRs and related downstream signaling and shows various effects on broad spectrums of important biological systems, such as transcriptional activity of NF-kB, secretion of IFNs and inflammatory cytokines. Thus the pharmaceutical composition comprising the oligonucleotides of the present invention can be used against various diseases including, but not limited to, autoimmune diseases, inflammations, cancers, tumors, allergies, which are caused by the abnormality in the above mentioned systems.

The oligonucleotide of the present invention may comprise a chemical modification, as the inhibitory effect on the targets including TLRs shown by the present invention rather depends on sequence of the oligonucleotides, which is described as CxTy(CCT)nCm, wherein n denotes an integer from 2 to 50, or preferably 5-16, x denotes integer 0 or 1, y denotes integer 0 (only when x=0) or 1 (x can either be 0 or 1), and m denotes integer of 0, 1 or 2 (Sun et al., Clin Immunol, 2010, 134, 262-276; Zhang et al., International Immunopharmacol, 2012, 446-453; EP2154144, WO2014/082254) and a chemical modification to improve drug profiles is commonly used among a person skilled in the art.

The oligonucleotide in the present invention is partially phosphorothioated in the internucleotide linkage, wherein the non-bridging O is replaced by S. As has been reported, oligonucleotides are unstable in vivo due to the rapid degradation possibly caused by nucleases existing in the blood serum. Thus many attempts have been made to increase the stability of oligonucleotides allowing longer half-life in vivo, such as chemical modification or use of drug delivery tools to prevent the attack from serum nucleases. Among such chemical modification, phosphorothioation at the internucleotide modification has been utilized from the early period of nucleic acid drug development. However, such phosphorothioation also has been known for its toxicity, which caused to be an obstacle for the nucleic acid drug development. Meanwhile, the oligonucleotides in the present invention successfully reduce liver toxicity without major challenge in the activity and stability by reducing phosphorothioated linkages with specific patterns.

In one embodiment, the oligonucleotide of the present invention comprises various chemical modifications, in addition to phosphorothioation as above-mentioned, in the chemical residues corresponding to the ones in phosphodiester internucleic linkages, in sugars and/or in nucleobases in natural nucleic acids (DNA or RNA).

The chemical modifications for such oligonucleotides either with deoxyribonucleotides or ribonucleotides being used as pharmaceutical purposes have been extensively studied so far (Freier et al., Nuc Acid Res, 1997, 25, 4429-4443; Kuwahara et al., Molecules, 2010, 15, 5423-5444; Deleavey et al., Chemistry & Biology, 19, 937-954; Mutisya et al., Nucleic Acids Research, 2014, 42, 6542-6551; Sharma et al., Med. Chem. Commun. 2014, 5, 1454-1471).

Modification in the internucleotide linkages includes, but not limited to, phosphorothioate, phosphorodithioate, phosphonoacetate, methylphosphonate, methylphosphorothioate, methylphosphate, ethylphosphate, ethylphosphorothioate, boranophosphate, boranophosphorothioate, methylboranophosphate, methylboranophosphorothioate, methylboranophosphonate, phosphoramidite, phosphoramidate, phosphorodiamidate, phosphorothioamidate, phosphorothiodiamidate, sulfamate, dimethylenesulfone, sulfonate, sulfide, sulfonate ester, methyleneimino, oxalyl, thioacetamide, formacetal, thioformacetal, carboxylate ester, carboxamide, amide, triazol, imino and their derivatives.

Modification in sugar modification includes, but not limited to, (a) introduction of electronegative atom/substituent at the 2'-position of sugar moiety, (b) bicyclic formation in the sugar moiety by fusing extra ring, (c) modification in the pentose ring structure, and (d) introduction of spirocyclic structure to the carbon in the sugar ring (Sharma et al., Med. Chem. Commun. 2014, 5, 1454-1471). Modification in sugar moiety also includes conversion of nucleic acid to nucleic acid analogue such as Morpholino, peptide nucleic acid (PNA), locked nucleic acid/bridged nucleic acid (LNA, BNA), cyclohexenyl nucleic acid (HNA), and glycol nucleic acid and/or threose nucleic acid (TNA).

Modification in nucleobases includes, but not limited to, (a) modified pyrimidine bases, such as 5-propynyl U, 2-thio T, and N3-thioethyl T, and (b) modified bases, which can be used universally, such as 3-nitropyrrol, imidazole-4-carboxamide, and 5-nitroindole. It may also include modification in cytosine nucleobase to form cytosine analogue.

The above-mentioned chemical modifications in the present invention either can singularly occur or can occur at the same time with others or with natural nucleic acids.

The oligonucleotide constituting present invention can be obtained from existing nucleic acid sources (e.g., genomic or cDNA), but are preferably synthetic. The oligonucleotides of the invention can be synthesized by a variety of automated nucleic acid synthesizers available in the market. These oligonucleotides are referred to as synthetic oligonucleotides.

The oligonucleotide in this invention can either be single strand, double strand or the hybrid of single and double strand. They can also form circular structure by connecting 5' and 3' ends of the single molecule; more than one oligonucleotide of this invention can be connected by covalent bonding or through distinctive linkers either at 5' or 3' end to form tandemly-connected elongated structures or multivalent structures. The linkers are organic chemical compounds which are generally used by the person skilled in the art, including but not limited to glycerol, (S)-(−)-1,2,4-Butanetriol, 1,3,5-Pentanetriol, cis,cis-1,3,5-Cyclohexanetriol, cistrans-1,3,5-Cyclohexanetriol, 1,3,5-tris-(2-Hydroxyethyl)isocyanurate, Tetraethyleneglycol, and Hexaethyleneglycol and here can also be constituted with amino acids nucleotides and/or their derivatives. The oligonucleotide in this invention preferably has fully phosphorothioated (CCT)3, (CTC)3 or (TCC)3 motif or its truncated form connected by phosphodiester bond in the core structure, which can be interrupted in the middle by one or a few nucleotides by the change or the insertion of nucleotide(s), but needs to contain CCT, CTC, or TCC repeats from 2-50, or preferably 5-16, in a single molecule.

In one embodiment, the oligonucleotide of this invention can be used in combination with each other, with other oligonucleotides with similar mechanism of function, with other organic compounds, such as (poly)peptides/antibodies or nucleic acids/oligonucleotides, or inorganic compounds, such as cytotoxic agents, which are often used for improvement or modification of physical properties of drugs. Such combination can be generated either with or without covalent bonding.

"Oligonucleotide": An oligonucleotide means multiple nucleotides (i.e. molecules comprising a sugar (e.g. deoxyribose) linked to a phosphate group and to an exchangeable organic base, which is either a substituted pyrimidine (Py) (e.g., cytosine (C), thymine (T)) or a substituted purine (Pu) (e.g., adenine (A) or guanine (G)). The term oligonucleotide as used herein mainly refers to oligodeoxyribonucleotide (ODN), but not limited if functionally identical.

"Chemical modification": The oligonucleotide disclosed in the invention can encompass various chemical modifications in a phosphodiester internucleoside bridge, a ribose unit and/or a natural nucleoside base (cytosine, and thymine). The modifications can occur either during or after synthesis of the oligonucleotide. During the synthesis, modified bases can be incorporated internally or at its end. After the synthesis, the modification can be carried out using the active groups (via an amino modifier, via the 3' or 5' hydroxyl groups, or via the phosphate group). The skilled person knows examples of chemical modifications. An oligonucleotide according to the invention may have one or more modifications, wherein each modification is located at a particular phosphodiester internucleoside bridge and/or at a particular ribose unit and/or at a particular natural nucleoside base position in comparison to an oligonucleotide of the same sequence, which is composed of natural DNA. The chemical modification includes "back bone modification" of the oligonucleotide of the invention. As used herein, the modified back bone of the oligonucleotide of the invention includes, but not limited to the "phosphorothioate backbone" that refers to a stabilized sugar phosphate backbone of a nucleic acid molecule in which non-bridging phosphate oxygen is replaced by sulfur. Other back bone modifications denote the modification with nonionic DNA analogues, such as alkyl- and aryl-phosphonates (in which the charged phosphonate oxygen is replaced by an alkyl or aryl group), phosphodiester and alkylphosphotriesters, in which the charged oxygen moiety is alkylated. The chemical modification also includes the base substitutions of the oligonucleotide disclosed in the invention. The substituted bases include but are not limited to cytosine, thymine, and other structurally-related naturally or non-naturally occurring nucleobases. The chemical modification of the oligonucleotide of the invention further includes the modification of the bases of the oligonucleotide. A modified base is any base which is chemically distinct from the naturally occurring bases typically found in DNA such as T, C, G and A, but which share basic chemical structures with these naturally occurring bases. The oligonucleotide of the invention can be modified by using cytidine derivatives and/or thymidine derivatives. The term "cytidine derivative" refers to a cytidine-like nucleotide (excluding cytidine) and the term "thymidine derivative" refers to a thymidine-like nucleotide (excluding thymidine). In addition, the oligonucleotides of the invention can be chemically modified by linking a diol, such as tetraethyleneglycol or hexaethyleneglycol, at either or both termini of the oligonucleotide.

"Immune-mediated disorder": An immune-mediated disorder is a disease caused by an unwanted immune response in a subject. The disorder includes autoimmune disease, graft rejection, hypersensitivity, diseases associated with the over-stimulation of host's immune system by microbes. The immune-mediated disorder can also be categorized based on the physiological pathway affected in the disease, such as a disease associated with TLR activation (TLR-mediated disease, TLR9-mediated diseases, TLR7 and/or 8-mediated disease), NF-kB-mediated disease, interferon-mediated disease, or inflammatory cytokine-mediated disease. The oligonucleotide disclosed in the invention can be used as a remedy to treat the immune-mediated disorder as above-mentioned.

"Immune response": A response of a cells of the immune system, such as a B cell, T cell, natural killer cell, dendritic cell, neutrophil and macrophage to a stimulus. The response includes innate immune response and adaptive (specific or acquired) immune response. The adaptive (specific or acquired) immune response includes humoral immune response and cellular immune response.

"Prevent or treat immune-mediated disorder": As used herein, prevent refers to preventing the full development of an immune-mediated disorder in a subject; treat refers to a therapeutic intervene in a subject so as to ameliorate a sign or symptom of, halt the progression of, or eliminate pathological condition of the immune-mediated disorder.

"Subject": As used herein, a subject refers to a human or non-human vertebrate. Non-human vertebrates are non-human primates, livestock animals and companion animals. The oligonucleotide of the invention can be administered to prevent or/and treat immune-mediated disorder in a subject.

"Autoimmune diseases": The term "autoimmune disease" refers to a disease caused by a breakdown of self-tolerance such that the adaptive and innate immune system responds to self-antigens and mediates cell and tissue damage. Autoimmune diseases are frequently characterized by their involvement of single organ or single cell-types, or involvement of multiple organs or tissue systems. Autoimmune diseases have also been referred to as "collagen," or "collagen-vascular" or "connective tissue" diseases. Autoimmune disorders are frequently associated with hypersensitivity reactions. The oligonucleotides of this invention can be useful for treating and/or preventing various types of autoimmune diseases. Specifically, non-limiting examples of autoimmune disorders are systemic lupus erythematosus, insulin-dependent (type I) diabetes mellitus, inflammatory arthritis, rheumatoid arthritis, multiple sclerosis, autoimmune hepatitis, chronic aggressive hepatitis, autoimmune hemolytic anemia, autoimmune thrombocytopenia, autoimmune atrophic gastritis of pernicious anemia, autoimmune encephalomyelitis, autoimmune orchitis, acquired hemophilia, ankylosing spondylitis, antiphospholipid syndrome, Behcet's disease, cardiomyopathy, chronic inflammatory demyelinating polyneuropathy, cicatricial pemphigoid, cold agglutinin disease, polymyositisdermatomyositis, discoid lupus, sympathetic ophthalmia, essential mixed cryoglobulinemia, fibromyalgia, fibromyositis, Guillain-Barre syndrome, idiopathic pulmonary fibrosis, idiopathic thrombocytopenic purpura, IgA nephropathy, juvenile arthritis, systemic sclerosis, polyarteritis nodosa, polychondritis, dermatomyositis, primary agammaglobulinemia, primary biliary cirrhosis, hyperimmunoglobulin E syndrome, progressive systemic sclerosis, psoriasis, Reiter's syndrome, sarcoidosis, stiff-man syndrome, uveitis, vasculitis, vitiligo, Hashimoto's thyroiditis, Goodpasture's disease, pernicious anemia, Addison's disease, Sjogren's syndrome, myasthenia gravis, Grave's disease, allergic encephalomyelitis, glomerulonephritis, microscopic polyangiitis, Wegener's granulomatosis, autoimmune thyroid diseases, juvenile idiopathic arthritis, giant cell arteritis, ulcerative colitis, Crohn's disease and the like (Davidson, Engl J Med, 2001, 345, 340-350; Delgado-Vega et al., Arthritis Research & Therapy 2010, 12/S2). DNA or RNA released from DNA- or RNA-containing microbes can stimulate the production of autoantibody specific to self DNA- or RNA-containing complexes and consequently lead to many of the autoimmune diseases described above, including but not limited to SLE.

"Graft rejection": The graft rejection is an immune-mediated disorder caused by organ or tissue transplantation; transplantation means the transfer of transplants (grafts) from a donor to a recipient. Grafts are the living cells, tissues, or organs transplanted from a donor to a recipient. An autograft is a graft of one's own tissue transferred from one location to another; a syngeneic graft (isograft) is a graft between identical twins; an allogeneic graft (homograft) is a graft between genetically dissimilar members of the same species; and a xenogeneic graft (heterograft) is a transplant between members of different species. When a subject is the recipient of an allogeneic graft or a xenogeneic graft, the body can produce an immune response against the donor tissue. In this situation, there is a clear need to suppress the immune response, in order to avoid rejection of the graft (Goldsby et al., Immunology, Fifth Edition, 2003, W.H. FREEMAN AND COMPANY). The oligonucleotides of the present invention are useful when administered for the prevention of the graft rejection. Examples of the grafts are heart, kidney, liver, medulla ossium, skin, cornea, lung, pancreas, intestinum tenue, limb, muscle, nervus, duodenum, small-bowel, pancreatic-islet-cell, and the like. In some case, the recipient may be an animal as defined in "subject" of the invention.

"Hypersensitivity": A hypersensitivity is referred to the disorders wherein tissue injury occurs as a result of a humoral or cell-mediated response to antigens of endogenous or exogenous origin and has been classified into four types. Type I hypersensitivity (frequently referred to as anaphylactic, immediate-type, atopic, reaginic, IgE-mediated hypersensitivity reactions or allergy) generally result from the release of pharmacologically active substances such as histamine, slow-reacting substance of anaphylaxis (SRS-A), and eosinophilic chemotactic factor (ECF) from IgE-sensitized basophils and mast cells after contact with a specific exogenous antigen. Type I hypersensitivity includes, but not limited to, allergic extrinsic asthma, seasonal allergic rhinitis and systemic anaphylaxis. Type II hypersensitivity (also referred as cytotoxic, cytolytic complement-dependent or cell-stimulating hypersensitivity reaction) results when antibody reacts with antigenic components of cells or tissue elements or with an antigen or hapten, which has become intimately coupled to cells or tissue. Type II hypersensitivity includes, but not limited to, autoimmune hemolytic anemia, erythroblastosis fetalis and Goodpasture's disease. Type III hypersensitivity (also referred to as toxic complex, soluble complex, or immune complex hypersensitivity reactions) results from the deposition of soluble circulating antigen-antibody complexes in vessels or in tissues, with accompanying acute inflammatory reactions at the site of immune complex deposition. Type III hypersensitivity includes, but not limited to, Arthus's reaction, serum sickness, systemic lupus erythematosus, and certain types of glomerulonephritis. Type IV hypersensitivity (frequently called cellular, cell-mediated, delayed, or tuberculin-type hypersensitivity reactions) are caused by sensitized T-lymphocytes which result from contact with a specific antigen. Type IV hypersensitivity includes, but not limited to, contact dermatitis and allograft rejection (Goldsby et al., Immunology, Fifth Edition, 2003, W.H. FREEMAN AND COMPANY).

"Diseases associated with the over-stimulation of host's immune system by microbes": Microbe invasion, if severe, sometimes can cause systemic inflammatory response in a subject, leading to diseases associated with the over-stimulation of host's immune system by microbes. The events in the development of the diseases, such as in the case of influenza A (H5N1) or bacterial infection, include the significantly elevated blood levels of TNFa, IL-1, IL-6, IL-12, IFNa, IFNb, IFNg, chemokines IFN-inducible protein 10, monocyte chemoattractant protein 1, IL-8, IL-lb, and monocyte chemoattractant protein 1. Such responses can result in cytokine-mediated lethal shock that is responsible in part for the sepsis, ARDS, and multiorgan failure observed in many patients (The Writing Committee of the World Health Organization (WHO) Consultation on Human Influenza A/H5, N Engl J Med, 2005, 353, 1374-85). The significantly elevated blood level of cytokines following microbe infection is termed by hypercytokinemia (hypercytokinaemia) or a cytokine storm. The research suggested that patients who contract bird flu or SARS may need drugs that suppress the immune response in addition to anti-viral drugs in order to suppress the cytokine elevated symptoms. Thus, the oligonucleotide of the invention can be used to treat and/or prevent the diseases associated with the stimulation of host's immune system by microbes in a subject. The microbes causing the diseases includes, but not limited to, viruses, bacteria, fungi, parasites and etiological agents of Spongiform encephalopathies. The virus that cause the diseases associated with the over-stimulation of host's immune system by microbes include: SARS CoV, influenza viruses, avian flu virus, HIV-1, polio viruses, hepatitis A virus; enteroviruses, human Coxsackie's viruses, rhinoviruses, echoviruses, equine encephalitis viruses, rubella viruses, dengue viruses, encephalitis viruses, yellow fever viruses, corona viruses, vesicular stomatitis viruses, rabies viruses, Ebola viruses, parainfluenza viruses, mumps virus, measles virus, respiratory syncytial virus, influenza viruses, Hantan viruses, bunga viruses, phleboviruses, Nairo viruses, hemorrhagic fever viruses; reoviruses, orbiviruses and rotaviruses, Hepatitis B virus, parvoviruses, papilloma viruses, polyoma viruses, adenoviruses, herpes simplex virus (HSV) 1 and HSV-2, varicella zoster virus, cytomegalovirus (CMV), herpes viruses, variola viruses, vaccinia viruses, pox viruses, African swine fever virus, the etiological agents of Spongiform encephalopathies, delta hepatitis virus, Hepatitis C virus, foot and mouth disease virus and avian flu virus. The bacteria that can cause the diseases associated with the over-stimulation of host's immune system by microbes include: *Helicobacter pyloris, Borelia burgdorferi, Legionella pneumophilia, Mycobacteria* sps (such as. *M. tuberculosis, M. avium*, M. E *intracellulare, M. kansasii, M. gordonae*), *Staphylococcus aureus, Neisseria gonorrhoeae,*

*Neisseria meningitidis, Listeria monocytogenes*, Group A *Streptococcus*, Group B *Streptococcus, Streptococcus, Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelii*. The fungi that can cause the diseases associated with the over-stimulation of host's immune system by microbes include, but not limited to, *Cryptococcus neoformans, Histoplasma capsulatum, Coccidioides immitis, Blastomyces dermatitidis, Chlamydia trachomatis, Candida albicans*. The parasites that can cause the diseases associated with the over-stimulation of host's immune system by microbes include: *Plasmodium falciparum* and *Toxoplasma gondii*.

"Toll-like receptor (TLR)-mediated diseases": A Toll-like receptor (TLR)-mediated disease means an immune mediated disorder related to the activation of members of the TLR family. The disease includes, but not limited to, sepsis associated with the activation of TLR4 by lipopolysaccharide (LPS), dilated cardiomyopathy associated with the activation of TLR2, 3, 4, 9, diabetes associated with the activation of TLR2,3,4,9, experimental autoimmune encephalomyelitis associated with the activation of TLR3, age-related macular disease associated with the activation of TLR3 (Patel et al., Mol Cell Neurosci, 2014, 63, 38-48), systemic lupus erythematosus associated with the activation of TLR9, atherosclerosis associated with the activation of TLR4, asthma associated with the activation of TLR4 by LPS, chronic obstructive pulmonary disease associated with the activation of TLR4, EAE associated with the activation of TLR4 and organ failure associated with the activation of TLR4 (Liew et al., Nature Review Immunology, 2005, 5, 446-458). CpG-containing DNA (a TLR9 agonist) derived from a nucleic acid-containing infectious agent could be identified from SLE serum that induces an efficient immune response dominated by IFNa secretion that is thought to contribute the development of SLE. The oligonucleotides of the present invention can be administered for treating and/or preventing the Toll-like receptor (TLR)-mediated diseases including but not limited to SLE in a subject.

"TLR9-mediated diseases": The term "TLR-9-mediated diseases" denotes diseases involving uncontrolled TLR9 expression and/or the activation of the TLR9 signaling, which are considered to be the causes of the symptoms and such diseases include but not limited to systemic lupus erythematosus, IgA nephropathy, periodontitis, sclerosing cholangitis, multiple sclerosis, inflammatory bowel disease, graft-versus-host disease, anti-neutrophil cytoplasmic antibody (ANCA) associated vasculitides (AAV), Fulminant type 1 diabetes (FT1D), end-stage renal disease, Acute pancreatitis (AP), granulomatosis with polyangiitis (GPA), dry eye disease, Wiskott-Aldrich syndrome, idiopathic pulmonary fibrosis, Cystic fibrosis, chronic rhinosinusitis, rheumatoid arthritis (RA), Sjogren's syndrome, pains, preterm labor and preeclampsia.

"TLR7 and/or 8-mediated diseases": The term "TLR7 and/or 8-mediated disease" denotes disease involving uncontrolled TLR7 and/or 8 overexpression and/or overactivation of the TLR7 and/or 8 signaling. Those phenomena are considered to be a good target for the treatment of diseases including, but not limited to systemic lupus erythematosus, lupus nephritis (Smith, Curr Opin Nehrol Hypertens, 2009, 18, 189), multiple sclerosis (Gambuzza et al., J Neuroimmunol, 2011, 239, 1-12), Type I diabetes, rheumatoid arthritis (RA), Sjogren's syndrome, Behcet's syndrome (Hatemi et al., Clin Exp Rheumatol, 2015, 33 (6 Suppl 94), 3-14), asthma (Tang et al., Respirology, 2015, October 18. doi: 10.1111/resp.12657. [Epub ahead of print])

"NF-kB-mediated disease": The term "NF-kB-mediated disease" denotes disease involving uncontrolled overactivation of NF-kB and affecting downstream gene expression. It includes, but not limited to rheumatoid arthritis, gastritis and inflammatory bowel disease, Allergies, Headaches, Pain, Complex Regional Pain Syndrome, Cardiac Hypertrophy, Muscular Dystrophy, Muscle wasting, Catabolic disorders, type I diabetes, type II diabetes, Fetal Growth Retardation, Hypercholesterolemia, Atherosclerosis, Heart Disease, Chronic Heart Failure, Ischemia/reperfusion, Stroke, Cerebral aneurysm, Angina Pectoris, Pulmonary Disease, Cystic Fibrosis, Acid-induced Lung Injury, Pulmonary hypertension, Chronic Obstructive Pulmonary Disease (COPD), Hyaline Membrane Disease, Kidney Disease, Glomerular Disease, Alcoholic Liver Disease, Leptospirosis renal disease, Gut Diseases, Peritoneal endometriosis, Nasal sinusitis, Anhidrotic Ectodermal Dysplasia-ID, Behcet's disease, Incontinentia pigmenti, Tuberculosis, Asthma, Arthritis, Crohn's Disease, Ocular Allergy, Glaucoma, Appendicitis, Paget's Disease, Pancreatitis, Periodontitis, Endometriosis, Inflammatory Lung Disease, Sepsis, Sleep apnea, Antiphospholipid Syndrome, Lupus, Lupus nephritis, Chronic Disease Syndrome, Familial Mediterranean Fever, Hereditary Periodic Fever Syndrome, Parkinson Disease, Multiple Sclerosis, Rheumatic Disease, Alzheimer's Disease, Amyotrophic lateral sclerosis, Huntington's Disease, Cataracts, chronic inflammatory demyelinating polyneuropathy, *Helicobacter pylori*-associated gastritis, Systemic inflammatory response syndrome and cancers (http://www.bu.edu/nf-kb/physiological-mediators/diseases/; Tak et al., J Clin Invest, 2001, 107, 7-11).

"interferon-mediated disease": It is caused by the overproduction of interferons and/or the overactivation of interferon-downstream genes, which includes but not limited to systemic lupus erythematosus, psoriasis, Sjogren's syndrome, rheumatoid arthritis (RA), scleroderma, inflammatory arthritis, type 1 diabetes, inflammatory bowel disease, multiple sclerosis, Graves' disease, microscopic polyangiitis, Wegener's granulomatosis, autoimmune thyroid diseases, juvenile idiopathic arthritis, giant cell arteritis, ulcerative colitis, and Crohn's disease (Delgado-Vega et al., Arthritis Research & Therapy, 2010, 12/S2).

"Inflammatory cytokine-mediated inflammation disease": it is induced by inflammatory cytokine, such as TNFa, IFNa, IL-1, IL-6, leukemia inhibitory factor (LIF), oncostatin M (OSM) and/or IL-12, which overactivates immunity through downstream signaling pathways of those cytokines. Inflammatory cytokine also activates downstream prostaglandin production, which is involved in the pain formation under disease condition. The diseases induced by such inflammatory cytokines show inflammatory response, as revealed by the hallmarks, such as swelling, redness, fever, pain and loss of function. Chronic inflammation may also cause fibrosis related to a wound-healing reaction, which can results in interference with normal tissue functions. Fibrosis includes but not limited to pulmonary fibrosis, liver cirrhosis, cardiac fibrosis, and cystic fibrosis. Chronic inflammation may also cause granuloma, which is an uncontrolled inflammation mass constituted with activated macrophages (epithelioid cells) (Goldsby et al., Immunology, Fifth Edition, 2003, W.H. FREEMAN AND COMPANY).

"CpG ODN": It has been documented that TLR9 agonist activates both innate and adaptive immune response (Krieg, Nature Reviews Drug Discovery, 2006, 5. 471-484). CpG containing oligonucleotides (CpG ODN) is a TLR9 agonist (Klinman, Nat. Rev., Immunol, 2004, 4, 249-258). Based on the functional characteristics, CpG ODNs are divided into three types (Ito et al., Blood, 2006, 107, 2423-2431). A-type CpG ODN activates human plasmacytoid dendritic cells (pDCs) to produce large amount of type I IFN (IFNa/β) and strongly activates natural killer cells (NK cells). B-type CpG ODN primarily activates B cells, resulting in their proliferation and antibody secretion. C-type CpG ODN shares the activities of both A- and B-type CpG ODN. As a TLR9 agonist, CpG ODN such as CpG 2216 or CpG 2006 or CpG 2395 can be endocytosed into a cellular compartment where they are exposed to and activate TLR9. In pDC, TLR9 activation initiate a rapid innate immune response that is characterized by the secretion of pro-inflammatory cytokines (IL-6, TNFa), the secretion of type I IFN and the secretion of IFN-inducible chemokines. Through both IFN-dependent and IFN-independent pathways, innate immune cells including natural killer (NK) cells, monocytes and neutrophils are secondarily activated by the pDC. B cells activated through TLR9 have a greatly increased sensitivity to antigen stimulation and efficiently differentiate into antibody-secreting cells, and therefore contributing to the adaptive immune response, especially humoral immune response. pDC activated through TLR9 secrete IFNa, which drives the migration and clustering of pDC to lymph nodes and other secondary lymphoid tissues where the pDC activates naive and memory T cells, assists the cross-presentation of soluble protein antigens to CD8+ cytotoxic T lymphocyte (CTL) and promotes strong TH1 biased cellular CD4 and CD8 T-cell responses. Based on the above mentioned findings, it is obvious that the agents that antagonize the activity of CpG ODN can be used to treat or prevent the immune-mediated disorder by inhibiting both innate and adaptive immune response.

"Pharmaceutically acceptable carrier": A pharmaceutically acceptable carrier denotes one or more solid or liquid filler, diluents or encapsulating substances that are suitable for administering the oligonucleotide of the invention to a subject. The carrier can be organic, inorganic, natural or synthetic. The carrier includes any and all solutions, diluents, solvents, dispersion media, liposome, emulsions, coatings, antibacterial and anti-fungal agents, isotonic and absorption delaying agents, and any other carrier suitable for administering the oligonucleotide of the invention and their use is well known in the art. The pharmaceutically acceptable carriers are selected depending on the particular mode of administration of the oligonucleotide. The parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Therapeutically effective amount": In order to treat or prevent an immune-mediated disorder, a therapeutically effective amount of an oligonucleotide of the present invention is administered to a subject. The "therapeutically effective amount" of one or more than one of the oligonucleotides means a sufficient amount of the oligonucleotide used to achieve a desired result of treating or preventing an immune-mediated disorder in a subject. The oligonucleotides of the present invention may be employed in pure form or in pharmaceutically acceptable carriers. Alternatively, the oligonucleotides may be administered as pharmaceutical compositions. The "amount" in the invention shall refer to a dose. The dose can be determined by standard techniques well known to those skilled in the art and can variously depend on the factors including, but not limited to the size or/and overall health of the subject or the severity of the disease symptom. Introduction of the oligonucleotide of the invention can be carried out as a single treatment or over a series of treatments. Subject doses of the oligonucleotide of the invention for the administration range from about 1 ug (micro gram) to 10 g per administration. Preferably, the doses range from 0.1 mg to 5 g. More preferably, the doses range from 0.3 mg to 3 g. The most preferably, the doses range from 1 mg to 1 g. The more preferred doses can be adjusted to provide the optimum therapeutic effect by those skilled in the art, for example, by the attending physician within the scope of appropriate medical judgement.

"Route of administration": For clinical use, the oligonucleotide of this invention can be administered alone or formulated in a pharmaceutical composition via any suitable route of administration that is effective to achieve the desired therapeutic result. The "route" of administering the oligonucleotide of the invention shall mean the enteral, parenteral and topical administration or inhalation. The enteral routes of administration of the oligonucleotide of the invention include oral, gastric, intestinal, and rectal. The parenteral route includes subcutaneous, intravenous, transdermal, sublingual, intranasal, transmucosal, pulmonary, vaginal, aerosol, intraocular, intratracheal, intrarectal, intraspinal, intramuscular, intraarticular, intraperitoneal, intracardiac, intraosseus, intrathecal, intravitreal, inhalational or topical administration. The topical route of administration of the oligonucleotide of the invention denotes the application of the oligonucleotide externally to the epidermis, to the buccal cavity and into the ear, eye and nose.

"Pharmaceutical composition": A pharmaceutical composition shall mean the composition comprising a therapeutically effective amount of the oligonucleotide of the invention with or without a pharmaceutically acceptable carrier. The pharmaceutical compositions can comprise one or more oligonucleotides of the invention. The composition includes but not limited to aqueous or saline solutions, particles, aerosols, pellets, granules, powders, tablets, coated tablets, (micro) capsules, suppositories, syrups, emulsions, suspensions, creams, drops and other pharmaceutical compositions suitable for use in a variety of drug delivery systems. The compositions may be administered parenterally, orally, rectally, intravaginally, intraperitoneally, topically (in a dosage form as powders, ointments, gels, drops or transdermal patch), bucally, or as an oral or nasal spray. In all cases, the composition must be sterile and stable under the conditions of manufacture and storage and preserved against the microbial contamination. Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. The oligonucleotide of the invention can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. The buffer solution includes sodium citrate-citric acid and sodium phosphate-phosphoric acid, and sodium acetate-acetic acid buffers. For oral administration, the composition will be formulated with edible carriers to form powders, tablets, pills, dragees, capsules, liquids, gels, syrups, slurries, suspensions and the like. For a solid composition, conventional non-toxic solid carrier can include pharmaceutical grades of mannitol, lactose, starch, or magnesium stearate. For buccal administration, the composition will be tablet or lozenge in conventional manner. For inhalation, the composition will be an aerosol spray from pressurized pack, a nebulizer, or a dry powder and can be selected by one of skill in the art. In some cases, in order to prolong the effect of the oligonucleotide of the invention, the oligonucleotides of the invention are also suitably administered by sustained-release systems. The oligonucleotide of the invention can be used in a liquid suspension of crystalline or amorphous material with poor water solubility to slow the releasing of the oligonucleotide. Alternatively, delayed releasing of a parenterally administered drug form of the oligonucleotide is accomplished by dissolving or suspending the oligonucleotide in hydrophobic material (such as an acceptable oil vehicle). Injectable depot form is made by entrapping the oligonucleotide in liposomes or microemulsions or other biodegradable semi-permeable polymer matrices such as polylactide-polyglycolide, poly (orthoesters) and poly (anhydrides).

"Active ingredients": The oligonucleotides of the invention can be used alone, in combination with themselves, in a pharmaceutically acceptable carrier, in combination with one or more additional active ingredients. The administration of the oligonucleotide of the invention and additional active ingredients can be sequential or simultaneous. The active ingredients include non-steroidal anti-inflammatory agents, steroids, nonspecific immunosuppressive agent, biological response modifier, chemical compound, small molecule, nucleic acid and TLR antagonists. The active ingredients also denote the agents that suppress the immune activation by antagonizing chemokines, by inducing the generation of regulatory T cells (CD4+CD25+ T cells), by inhibiting a complement, matrix metalloproteases and nitric oxide synthase, by blocking costimulatory factors and by inhibiting the signaling cascades in the immune cells. The non-steroidal anti-inflammatory agent includes, but unlimited to, diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib and rofecoxib. The steroid includes, but unlimited to, cortisone, dexamethasone, hydrocortisone, methylprednisolone, prednisolone, prednisone, and triamcinolone. A nonspecific immunosuppressive agent means the agent used to prevent the development of immune-mediated disorder. The nonspecific immunosuppressive agent includes but not limited to cyclophosphamide, cyclosporine, methotrexate, steroids, FK506, tacrolimus, mycophenolic acid and sirolimus. The biological response modifier includes a small molecule, a recombinant protein or monoclonal antibody targeting molecules as following, but not limited to:
i) Targeting IL-1: kineret/Anakinra and rilonacept/Arcalyst
ii) Targeting TNFa signaling: etanercept/Enbrel, infliximab/Remicade, and golimumab/Simponi iii) Targeting IL-6: tocilizumab/Actemra, siltuximab/Sylvant, sirukumab, and olokizumab iv) Targeting IFNa: sifalumab and rontalizumab
v) Targeting BAFF: belimumab/Benlysita, blisimod, and atacicept
vi) Targeting IL-17: secukinumab/Cosentyx, brodalumab/Lumicef, and ixekizumab/Talz
vii) Targeting IL-23 or IL-12/23: ustekinumab/Stelara, guselkumab, briakinumab, and tildrakizumab
viii) Inhibiting JAK (Janus Kinase): ruxolitinib/Jakafi, and Tofacitinib/Xeljanz
The agents also include Interferon beta-1a, IL-1β and TGF or their derivatives. They also include a monoclonal antibody/a recombinant protein to eliminate certain immune cells, such as B cells (rituximab/Rituxan, Eptratuzumab) and, protein to suppress lymphocyte activation, such as abatacept/Orencia, natalizumab/Tysabri and Daclizumab/Zimbryta.

"Delivery vehicle": The oligonucleotides of the invention can be administered in/with a delivery vehicle or in a form linked with a vehicle. The vehicle includes, but not limited to, sterol (e.g., cholesterol), cochleates, emulsomes, ISCOMs; a lipid (e.g., a cationic lipid, anionic lipid), liposomes; ethylene glycol (PEG); live bacterial vectors (e.g., *Salmonella, Escherichia coli, bacillus* Calmette-Gurin, *Shigella, Lactobacillus*), live viral vectors (e.g., Vaccinia, adenovirus, Herpes simplex), virosomes, virus-like particles, microspheres, nucleic acid vaccines, polymers (e.g., carboxymethylcellulose, chitosan), polymer rings and a targeting agent that recognizes target cell by specific receptors.

"Pegylation": Pegylation is the process of covalent attachment of poly (ethylene glycol) polymer chains to another molecule, normally a drug or therapeutic protein. Pegylation is routinely achieved by incubation of a reactive derivative of PEG with the target agent. The pegylated agent can "mask" the agent from the host's immune system, and increase the hydrodynamic size of the agent which prolongs its circulatory time. The oligonucleotides of the invention can be pegylated.

Unless otherwise noted, all terms in the invention have the same meaning as commonly understood by one of ordinary skill in the art to which this disclosure belongs. The singular terms "a," "an," and "the" include plural referents unless context indicates otherwise. Similarly, the word "or" is intended to include "and" unless the context indicates otherwise. The term "a few" means numeral from 2 to 3 in this description. The term "several" means numeral from 2 to 6 in this description. In case of conflict, the present specification, including explanations of terms, will control. In addition, the materials, methods and examples are illustrative only and not intended to be limiting. Treat, treating or treatment shall have the same meaning without concerning the grammar. Similarly, prevent, preventing or prevention shall have the same meaning without concerning the grammar.

EXAMPLES

The invention will be described in more detail in the following Examples. Meanwhile, the invention is not limited to these Examples. In these Examples, herein, experiments using commercially available kits and reagents were done according to the attached protocols, unless otherwise stated. The skilled person will appreciate that the oligonucleotides of the present invention can easily be applied to treat an immune-mediated disorder. The present invention will now be demonstrated by the following non-limiting examples.

TLR9 stimulatory oligonucleotides used in the following examples were CpG2395 (5'-TCGTCGTTTTCG-GCGCGCGCCg-3', SEQ ID NO.: 43), CpG2216 (5'-GGgggacgatcgtcGGGGGg-3', SEQ ID NO.: 44), which were all single strand DNA and were synthesized at Hokkaido System Science Co. Ltd (Sapporo, Japan), where the capital case letters in the oligonucleotides denote phosphorothioated nucleotides and the lower case letters, nucleotides with phosphodiester bonds at their 3' end. TLR7 or 8 stimulation was achieved by the addition of Gardiquimod (Invivogen). All the oligonucleotides of this invention used in the example were also single strand DNA, synthesized at Hokkaido System Science Co. Ltd (Sapporo, Japan). Those used in the examples are oligonucleotides which can be described as CxTy(CCT)nCm, where n is an integer from 2-50, or preferably 5-16, x denotes integer 0 or 1, y denotes integer 0 (only when x=0) or 1 (x can either be 0 or 1), and m is 0, 1 or 2, which are fully or partially phosphorothioated at the internucleotide linkages. The sample oligonucleotides described in the examples are as following:

```
CCT8PS (23 phosphorothioated bonds):
                              (SEQ ID NO.: 45)
5'-CCTCCTCCTCCTCCTCCTCCTCCt-3', CCT12PO (0 phosphorothioated bonds):
                              (SEQ ID NO.: 15)
5'-cctcctcctcctcctcctcctcctcctcctcctcct-3'

CCT12PS (35 phosphorothioated bonds):
                              (SEQ ID NO.: 46)
5'-CCTCCTCCTCCTCCTCCTCCTCCTCCTCCTCCTCCt-3'

CCT12-1 (30 phosphorothioated bonds):
                              (SEQ ID NO.: 25)
5'-CCTCCtCCTCCtCCTCCTCCTCCtCCTCCTCCTCCt-3'

CCT12-2 (32 phosphorothioated bonds):
                              (SEQ ID NO.: 26)
5'-CCTCCTCCtCCTCCTCCTCCtCCTCCTCCtCCTCCTCCt-3'

CCT12-3 (31 phosphorothioated bonds):
                              (SEQ ID NO.: 27)
5'-CCTCCtCCTCCTCCtCCTCCTCCtCCTCCTCCtCCt-3'

CCT12-4 (32 phosphorothioated bonds):
                              (SEQ ID NO.: 47)
5'-CCTCCtCCTCCTCCTCCtCCTCCTCCTCCtCCTCCt-3'

CCT12-5 (31 phosphorothioated bonds):
                              (SEQ ID NO.: 48)
5'-CCtCCTCCtCCTCCTCCTCCtCCTCCTCCTCCtCCt-3', TCC12PO (0 phosphorothioated bond):
                              (SEQ ID NO: 20)
5'-tcctcctcctcctcctcctcctcctcctcctcctcc-3'

TCC12PS (35 phosphorothioated bonds):
                              (SEQ ID NO: 49)
5'-TCCTCCTCCTCCTCCTCCTCCTCCTCCTCCTCCTCCc-3'

TCC12-6 (32 phosphorothioated bonds):
                              (SEQ ID NO.: 40)
5'-TCCTCCTCcTCCTCCTCcTCCTCCTCcTCCTCCTCc-3', TCC12-7 (32 phosphorothioated bonds):
                              (SEQ ID NO.: 50)
5'-TCCTCcTCCTCCTCCTCcTCCTCCTCCTCcTCCTCc-3', TCC6-1 (16 phosphorothioated bonds):
                              (SEQ ID NO.: 36)
5'-TCCTCCTCcTCCTCCTCc-3',
``` wherein the capital case letter denotes the base is phosphorothioate-modified in the internucleotide linkage at 3', and the lower case letter denotes that the base is un-modified. All reagents used to manipulate the oligonucleotides in the following examples were pyrogen-free.

Example 1

Stability of partially phosphorothioated oligonucleotides compared with oligonucleotides with normal phosphodiester linkage or phosphorothioated oligonucleotides Experimental Method Oligonucleotides (10 ng/uL) were incubated in distilled water (DW) with 20% (v/v) of human sera (Cosmo Bio, Cat.12181201) at 37° C. The solution containing oligonucleotide was collected after 1 day incubation and examined for the concentration of remaining undegraded oligonucleotides. The concentration of oligonucleotides in the solution was determined by the hybridization assay using complementary oligonucleotide of (CCT)12 or (TCC)12 as a probe, which only detects the ones with full-length oligonucleotides with (CCT)12 or (TCC)12 sequence.

Experimental Result

FIG. 1 shows the ratio of remaining intact oligonucleotide after 1 day incubation in the serum-containing medium; the ratio is shown by % compared to the concentration of the oligonucleotide at the beginning of the study. As shown in FIG. 1a, the CCT12PO with normal phosphodiester internucleotide bonds showed almost complete degradation in 1-day incubation, while fully phosphorothioated CCT12PS showed rather longer duration, which reveals the fast degradation of the oligonucleotide without internucleotide modification. As shown in the FIG. 1a, non-phosphorothioated oligonucleotide, CCT12PO showed rapid degradation under the presence of serum in the aqueous solution, meanwhile, the fully or partially phosphorothioated oligonucleotides (CCT12PS and CCT12-3) showed stable over 24 hours. FIG. 1b shows the stability of partially phosphorothioated (TCC)12 species. It was shown that while the oligonucleotide without phosphorothioation (TCC12PO) showed rapid degradation after 1-day incubation, the partially phosphorothioated oligonucleotide (TCC12-6) revealed increased stability as much as the fully phosphorothioated species with the same sequence (TCC12PS).

Example 2

In Vivo Toxicity Examination of the Oligonucleotide

Experimental Method

Oligonucleotides were dissolved in saline at 2 mg/ml and subcutaneously injected to mice (BALB/c) once every day at 100 uL/10 g body weight, which makes 20 mg/kg (mpk) for 7 consecutive days. Mice were examined for the body weight to see if the oligonucleotides show any effect on the weight. In the figures from 2a to 2c, the X-axis denotes the days from the first dosing (i.e. Day 0 is the first day of dosing; Day 6 is the last day of dosing). The mean of the body weight (3 animals in each group) is shown on Y axis by the ratio from the beginning of the study set to 100%.

On the next day of the last dosing (Day 7), the blood collected from the mice was subjected to biochemistry analysis to see the effect on markers showing liver damage, such as Alanine transaminase (ALT). FIGS. 2d and 2e show the concentrations of blood ALT on the Y axis. ALT is commonly measured clinically as a part of a diagnostic evaluation of hepatocellular injury, to determine liver health. In general, 10-40 IU/L is the standard reference range in any mammals such as human, cat, dog, mouse, rat and the like. The ALT ranges may vary, even among humans, depending on the conditions of the subject, such as age, sex and ethnicity; thus the toxicity of the target compound is generally evaluated by the comparison with reference obtained in the subject with similar background. In the present application, measurement of ALT was outsourced to Nagahama Lifescience Laboratory of Oriental Yeast Co., Ltd. And the measurement was conducted with the Laboratory Testing kit, L-type ALT J2 (Wako Pure Chemicals) in accordance with the manufacture's standard protocol. If the measured ALT value significantly exceeds that of the animal dosed with saline (Saline in FIGS. 2d and 2e), the subject is diagnosed to suffer from liver toxicity.

Experimental Result

As shown in the FIG. 2a, the mice dosed with saline did not show any decrease in body weight, while the ones dosed either with CCT8PS or CCT12PS showed significant decrease in the body weight, accompanied by a death of one animal in either of the dosing group due to the strong toxicity. Meanwhile, partially phosphorothioated oligonucleotides showed variable behavior among them (from FIGS. 2a to c), such that strong toxicity shown for CCT12-4 (FIG. 2b), CCT12-5, and TCC12-7 (FIG. 2c) revealed by the drastic decrease in the body weight, while no apparent toxicity was observed for CCT12-2, CCT12-3 (FIG. 2b), TCC6-1 and TCC12-6 (FIG. 2c). Among the group of mice dosed with TCC12-7, one mouse died in the course of administration revealing strong toxicity. Interestingly, even the oligonucleotides with the same ratio of phosphorothioation, such as CCT12-2 and CCT12-4, CCT12-3 and CCT12-5, and TCC12-6 and TCC12-7, showed difference in toxicity.

The mice were also examined on biochemical analysis on a day after the final administration (day 7, FIGS. 2d and 2e). The mice with toxic oligonucleotides, such as fully phosphorothioated CCT12PS or partially phosphorothioated CCT12-4 or TCC12-7 showed drastic increase in ALT. Meanwhile, dosing of some of the partially phosphorothioated oligonucleotides, such as CCT12-1, CCT12-2, CCT12-3 (FIG. 2d), and TCC12-6 (FIG. 2e) did not show increase in ALT, revealing the lack of liver damage as in the case of saline control-dosed animals.

In total, it was consequenced that the toxicity did not depend on the ratio or the number of phosphorothioated linkages in each molecule; among the 12 CCT-repeat oligonucleotides with 32 phosphorothioate bonds, CCT12-2 did not show any toxicity while CCT12-4 showed strong toxicity; among the 12 CCT-repeat oligonucleotides with 31 phosphorothioate bonds, CCT12-3 did not show any toxicity while CCT12-5 showed strong toxicity; among the 12-TCC repeat oligonucleotides with 32 phosphorothioate bonds, TCC12-6 did not show any toxicity while TCC12-7 showed strong toxicity.

The common feature among all the oligonucleotides with reduced toxicity is the structure of 3 CCT or TCC fully phosphorothioated stretches or its truncated stretches connected by phosphodiester linkage, while the oligonucleotides with toxicity commonly have at least 4 CCT or TCC fully phosphorothioated stretches.

Meanwhile, 20 mg/kg dose, examined in this example may be considered to be equivalent to 1.62 mg/kg in human when calculated by the dose conversion according the FDA guideline based on the Body Surface Area (Guidance for Industry, Estimating the Maximum Safe Starting Dose in Initial Clinical Trials for Therapeutics in Adult Healthy Volunteers, U.S. Department of Health and Human Services Food and Drug Administration, Center for Drug Evaluation and Research (CDER), July 2005), which makes single dosing of approximately 100 mg (in case of 60 kg body weight). Thus this study suggests that at least one-week succeeding daily dosing of 100 mg oligonucleotide of this invention is considered to be tolerable enough when it is applied to human and it also shows that even higher dosing will be allowed. The dosing schedule and the dosing level will be adjusted by the medical doctors or others skilled in the art.

Example 3

Inhibition of NF-kB Transcriptional Activity

Experimental Method

CAL-1/NF-kB-GFP cell line was established for monitoring the activity of NF-kB transcription factor in cell-based assays (WO2014/082254). Vector encoding the GFP reporter gene driven by the NF-kB consensus transcriptional response element was transfected into human plasmacytoid DC cell line; CAL-1 (human pDC cell lines, Maeda et al., Int J Hematol., 2005, 81, 148-54, JP5011520) by electroporation. Transfected cells were further selected with antibiotics. Then the CAL-1/NF-kB-GFP cells ($1\times10^5$/well) were plated in 96-well flat-bottomed plate (Costar) and cultured with TLR agonists and with or without oligonucleotides of this invention. The cells were incubated at 37° C. in a 5% $CO_2$ humidified incubator for 4 (TLR7/8) or 6 hours (TLR9). The change in NF-kB transcriptional activity was shown by the ratio of GFP-positive cells detected by flow cytometer (FACS Calibur, BD Bioscience Co., Ltd) as data from cells without inhibitors set to 100% (Medium). Activation of signaling downstream of TLR7/8 was achieved by the addition of Gardiquimod at 3 ug/ml for FIG. 3a (oligonucleotides, 0.1 uM) and 2 ug/ml for FIGS. 3b and 3c (oligonucleotides, 0.33 uM), and TLR9, by the addition of CpG2395 at 1 uM.

Experimental Result

In FIG. 3a, the horizontal axis denotes the ratio of luminescence driven by the active NF-kB, compared to the sample shown in the cells treated only with medium as 100% (Medium). As shown in the FIG. 3a, the partially phosphorothioated oligonucleotides (CCT12-1, 2, 3 and 4) showed inhibitory activity at the similar levels with fully phosphorothioated oligonucleotide, CCT12-PS. Thus the oligonucleotides shown here did not show changes in inhibitory activity against NF-kB transcriptional activity, regardless of decrease in phosphorothioation levels at internucleotide linkages. In the FIGS. 3b and 3c, it was also shown that the change in the pattern of phosphorothioation did not affect the inhibitory effect being revealed by the fact that the oligonucleotides with the same ratio of phosphorothioation (CCT12-3 and CCT12-5; TCC12-6 and TCC12-7) did not show significant difference in inhibitory effects against TLR7/8 or TLR9 activation.

Example 4

Inhibition of cytokine productions by the oligonucleotides in CAL-1 cells

Experimental Method

CAL-1 cells (seeded at $1\times10^5$/well) were incubated with TLR agonists (gardiquimod as TLR7/8 agonist, at 3 ug/ml for FIG. 4a or at 2 ug/ml for FIG. 4b; or CpG2395 as TLR9 agonist, at 1 uM) and with or without inhibitory oligonucleotides for 24 hours at 37° C. and the supernatant was collected by centrifugation. Then the cytokines, such as TNFa or IL-6, were examined by ELISA for the concentration in the medium. ELISA was conducted with following kits according to the manufactures' protocol: Human TNFa DuoSet ELISA (R&D Systems, Cat.Dy210), Human IL-6 DuoSet ELISA (R&D Systems, Cat.Dy206)

FIGS. 4a, 4b and 4c depict the production levels of TNFa or IL-6 shown by the ratio against the sample without inhibitory oligonucleotides, whose cytokine concentration in the medium set to be 100% (Medium). In the FIG. 4a, the oligonucleotides, CCT12PS, CCT12-1, CCT12-2, CCT12-3, and CCT12-4, were used at 0.1 uM for both TLR7/8 agonist or TLR9 agonist, and in the FIGS. 4b and 4c, the oligonucleotides, CCT12-3, CCT12-5, CCT12-6 and CCT12-7 were used at 0.037 uM for TLR7/8 agonist, or 0.011 uM for TLR9 agonist.

Experimental Result

As shown by FIG. 4a, all the oligonucleotides including partially phosphorothioated ones (CCT12-1, 2, 3 and 4) showed similar levels of inhibition in cytokine productions, induced either by TLR7/8 or TLR9, which reveals that the partial Phosphorothioation does not affect the inhibitory effect on cytokine productions. FIG. 4b showed that the inhibitory effect on the production of TNFa and IL-6 induced by Gardiquimod or CpG2395 was not affected by the change in phosphorothioation levels when compared between CCT12-3 and CCT12-5 or TCC12-6 and TCC12-7.

Example 5

Inhibition of IFNa by the oligonucleotides in human PBMC

Experimental Method

Human PBMCs collected from 2 healthy volunteer donors were incubated with a TLR9 agonist, CpG2216 at 1 uM and with or without inhibitory oligonucleotides at 37° C. for 24 hours and the IFNa in the supernatants was examined by ELISA.

The ELISA analysis on IFNa concentrations was conducted with Human IFNa Module Set (Bender MedSystems, Cat. BMS216MST) according to the manufacturer's protocol.

In the FIG. 5a (oligonucleotide at 0.03 uM) and b (oligonucleotide at 0.011 uM), the level of IFNa in each sample was shown as ratio against the IFNa production with TLR agonist, but without inhibitory oligonucleotides and the mean between the results from 2 donors was plotted on the Y axis.

Experimental Result

As shown in the FIG. 5a, IFNa production, induced by TLR9 agonist, was suppressed by any of the inhibitory oligonucleotides, either the ones with or without toxicity, revealing that the decrease in phosphorthioation does not affect the inhibitory effect of the oligonucleotides and even the oligonucleotides with same levels of phosphorothioation. The t-test result supported that there were not significant difference between CCT12PS and each partially phosphorothioated oligonucleotides (i.e. CCT12-1, CCT12-2, CCT12-3 or CCT12-4; each p-values are 0.3501, 0.5108, 0.3096, and 0.2922).

In the FIG. 5c, TCC12 species with different phosphorothioation patterns were compared in the suppression on IFNa production and the phosphorothioation patterns were found not to affect the activity of the oligonucleotides, which is supported by the p-value calculated by t-test showing no-significant difference between the results with TCC12-6 and TCC12-7 (p-value=0.4541).

In total, this invention offers the oligonucleotides to treat immune-mediated disorders which are more stable, but with less toxicity compared to the previous inventions. Interestingly, the oligonucleotides of this invention with small toxicity all commonly have the structure with the motif of fully phosphorothioated stretches of 3 CCT or TCC repeats and/or their truncated stretches connected by phosphodiester bonds in between (e.g. CCT12-1, CCT12-2, CCT12-3, TCC12-6, and TCC6-1), while the oligonucleotides with strong toxicity have larger (more than 3) fully-phosphorothioated stretches (e.g. CCT12-4, CCT12-5, TCC12-7, including CCT12PS and TCC12PS).

Consequently, the oligonucleotide in the present application can be effective for therapy of immune-mediated disorders in comparison with the prior arts, because the oligonucleotide can possess less toxicity, thereby enabling the increasing dose regimen of pharmaceutical composition comprising said oligonucleotide.

The invention claimed is:

1. A partially phosphorothioated oligonucleotide, wherein the nucleobase sequence of the oligonucleotide is 5'-CCTCCtCCTCCTCCtCCTCCTCCtCCTCCTCCtCCt-3' (SEQ ID NO:27), wherein a capital case letter denotes a nucleotide that is phosphorothioate-modified in the internucleotide linkage at 3', and a lower case letter denotes a nucleotide that is phosphodiester-un-modified in the internucleotide linkage at 3'.

2. The oligonucleotide according to claim 1, wherein said oligonucleotide comprises an additional chemical modification, wherein the additional chemical modification is other than phosphorothioation.

3. A pharmaceutical composition comprising the oligonucleotide according to claim 1 and a pharmaceutically acceptable carrier.

4. A partially phosphorothioated oligonucleotide, wherein the nucleobase sequence of the oligonucleotide is 5'-TCCTCCTCcTCCTCCTCcTCCTCCTCcTCCTCCTCc-3' (SEQ ID NO:40), wherein a capital case letter denotes a nucleotide that is phosphorothioate-modified in the internucleotide linkage at 3', and a lower case letter denotes a nucleotide that is phosphodiester-un-modified in the internucleotide linkage at 3'.

5. The oligonucleotide according to claim 4, wherein said oligonucleotide comprises an additional chemical modification, wherein the additional chemical modification is other than phosphorothioation.

6. A pharmaceutical composition comprising the oligonucleotide according to claim 4 and a pharmaceutically acceptable carrier.

* * * * *